United States Patent [19]

Brown et al.

[11] Patent Number: 5,162,308

[45] Date of Patent: Nov. 10, 1992

[54] PYRROLE CARBONITRILE AND NITROPYRROLE INSECTICIDAL, ACARICIDAL AND MOLLUSCICIDAL AGENTS AND METHODS FOR THE PREPARATION THEREOF

[75] Inventors: Dale G. Brown, Hopewell; Robert E. Diehl, Lawrenceville, both of N.J.; Gregory T. Lowen, Langhorne, Pa.; Donald P. Wright, Jr., Pennington, N.J.; Christine F. Kukel, Neshanic Station, N.J.; Rod A. Herman, West Pittsburg, Calif.; Roger W. Addor, Pennington, N.J.

[73] Assignee: American Cyanamid Company, Stamford, Conn.

[21] Appl. No.: 776,967

[22] Filed: Oct. 15, 1991

Related U.S. Application Data

[63] Continuation of Ser. No. 430,601, Nov. 6, 1989, abandoned, which is a continuation-in-part of Ser. No. 279,909, Dec. 5, 1988, abandoned.

[51] Int. Cl.$^5$ .................. A01N 43/36; A01N 55/00
[52] U.S. Cl. ........................... 514/63; 514/423; 514/426; 514/427
[58] Field of Search ............. 514/63, 423, 426, 427

[56] References Cited

U.S. PATENT DOCUMENTS

| | | | |
|---|---|---|---|
| 3,864,491 | 2/1975 | Bailey | 71/67 |
| 3,932,458 | 1/1976 | Bailey | 71/67 |
| 3,985,539 | 10/1976 | Bailey | 71/67 |
| 4,376,778 | 3/1983 | Ezaki et al. | 548/557 |
| 4,563,472 | 1/1986 | Inouye et al. | 514/381 |

FOREIGN PATENT DOCUMENTS

| | | |
|---|---|---|
| 0080051 | 6/1983 | European Pat. Off. |
| 0372982 | 6/1990 | European Pat. Off. |
| 88044146B | 10/1980 | Japan |
| 58062159A | 10/1981 | Japan |
| 2066816 | 7/1981 | United Kingdom |

OTHER PUBLICATIONS

Chem. Abstracts, 89:157172 (1978).
J. Antibiotics, 34(12):1569–1576 (Dec. 1981).
J. Med. Chem., 30:552 (1987).
Chem. Abstracts, 79:31775s (1973).
J. Org. Chem., 49 (21):4065–4067 (1984).
Can. J. Chem., 58:409–411 (1980).
Can. J. Chem., 59 (13):2673–2676 (1981).
Can. J. Chem., 62:1046–1050 (1984).
J. Hetrocyclic Chem., 7(5):1101–1108 (Oct. 1970).
Can. J. Chem., 37:2053–2058 (1959).
Br. J. Cancer, 37 (Suppl. III) 6:10 (1978).

Primary Examiner—Allen J. Robinson
Attorney, Agent, or Firm—John W. Hogan, Jr.

[57] ABSTRACT

There are provided certain insecticidal, acaricidal and molluscicidal pyrrole carbonitrile and nitropyrrole compounds and a method for controlling insects, acarids and mollusks therewith. The invention also provides a method for protecting growing plants from insect, acarid and mollusk attack by applying to said plants or the soil or water in which they are growing, an insecticidally, acaricidally or molluscicidally effective amount of a pyrrole carbonitrile or nitropyrrole compound. The present invention further relates to methods for the preparation of said pyrrole carbonitrile and nitropyrrole compounds.

13 Claims, No Drawings

PYRROLE CARBONITRILE AND NITROPYRROLE INSECTICIDAL, ACARICIDAL AND MOLLUSCICIDAL AGENTS AND METHODS FOR THE PREPARATION THEREOF

This is a continuation of application, Ser. No. 07/430,601, filed Nov. 6, 1989, abandoned, which is a continuation-in-part application of Ser. No. 07/279,909, filed Dec. 5, 1988, abandoned.

BACKGROUND OF THE INVENTION

There is a body of literature which discloses a variety of natural and synthetic pyrroles as antifungal and antibacterial agents. However, this literature appears to be devoid of any disclosure or suggestion that would lead one to believe that pyrrole carbonitriles and/or nitropyrroles could be effectively employed for the control of insects, acarids or mollusks, or for the protection of plants or crops from attack by these pests.

2,3-Dichloro-4-nitropyrrole is disclosed and its antibiotic effectiveness described in U.S. Pat. No. 4,376,778. The publication, Journal of Antibiotics 34 (12):1569 (1981) likewise describes the antibiotic activity of this compound and several other mono- and dichloro-3-nitropyrroles, including a 2,4,5-trichloro-3-nitropyrrole; however, no reference is made to any insecticidal, acaricidal or molluscicidal activity observed or indicated for such compounds. U.S. Pat. No. 4,563,472 discloses generically a series of compounds illustrated by the structure:

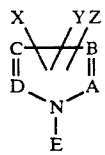

where E is a 2,3,3-triiodoallyl group or a 3-iodopropargyl group; A, B, C and D each individually represent a nitrogen atom or a carbon atom, and X, Y and Z may be a hydrogen atom, chlorine atoms, or a nitro group. These compounds have antifungal activity.

4,5-Dihalopyrrole-2-carbonitrile (Br and Cl) and their herbicidal properties are disclosed in U.S. Pat. No. 3,985,539. Certain nitropyrroles, dinitropyrroles, cyanonitropyrroles, and cyanodinitropyrroles, which include N-substitution by methyl, propyl, or hydroxyethyl groups, have been examines as radiosensitizers.

It is an object of the present invention to provide certain novel pyrrole carbonitrile and nitropyrrole compounds that are highly effective for controlling insects, acarina and mollusks. It is also an object of the invention to protect growing plants and crops from attach by insects, acarina and mollusks, by contacting said pests, or their food supply, breeding grounds or habitat with an insecticidally, acaricidally or molluscicidally effective amount of a pyrrole carbonitrile or nitropyrrole.

These and other objectives of the invention will become more apparent from the detailed description thereof set forth below.

SUMMARY OF THE INVENTION

The present invention relates to methods and compositions for controlling insects, acarids and mollusks. It also relates to methods and compositions for protecting agronomic crops, both growing and harvested, from attack by insects, acarids and mollusks, by applying to said crops or the locus in which they are growing or stored, an insecticidally, acaricidally or molluscicidally effective amount of a pyrrole carbonitrile or nitropyrrole having the structure:

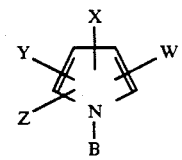

wherein
W is CN or $NO_2$;
X is CN, Br, Cl, I or $CF_3$;
Y is H, Br, Cl, I or $CF_3$;
Z is H, Br, Cl or I; and
B is

hydrogen,
$C_1-C_6$ alkyl optionally substituted with one to three halogen atoms,
one tri($C_1-C_4$ alkyl)silyl,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
one $C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group,
$C_3-C_6$ alkynyl optionally substituted with one to three halogen atoms or one phenyl group,
or cyano
R is $C_1-C_6$ alkyl optionally substituted with one to three halogen atoms,
one hydroxy,
one cyano, one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms, one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups, or
one benzyloxycarbonyl group optionally substituted on the phenyl ring with one to three halogen atoms, one to three $C_1$-$C_4$ alkyl groups or one to three $C_1$-$C_4$ alkoxy groups,
$C_3$-$C_6$ alkenyl optionally substituted with one to three halogen atoms or one phenyl group,
$C_3$-$C_6$ alkynyl optionally substituted with one to three halogen atoms or one phenyl group,
phenyl optionally substituted with one to three halogen atoms, one or two $C_1$-$C_4$ alkyl groups, one or two $C_1$-$C_4$ alkoxy groups, $CF_3$, CN, $NO_2$, di($C_1$-$C_4$ alkyl)amino or $C_1$-$C_4$ alkanoylamino,
phenoxy optionally substituted with one to three halogen atoms, one or two $C_1$-$C_4$ alkyl groups, one or two $C_1$-$C_4$ alkoxy groups, $CF_3$, CN or $NO_2$, di($C_1$-$C_4$ alkyl)amino or $C_1$-$C_4$ alkanoylamino,
$C_1$-$C_6$ alkoxy optionally substituted with one to three halogen atoms,
$C_2$-$C_6$ alkenyloxy optionally substituted with one to three halogen atoms,
di($C_1$-$C_4$ alkyl)amino,
N-($C_1$-$C_4$ alkyl)-N-phenylamino or -N-halophenylamino, or $C_3$-$C_6$ polymethyleneimino.

The present invention also provides bait compositions that contain a molluscicidally effective amount of a pyrrole carbonitrile or nitropyrrole compound having the formula I structure shown above. Moreover, it should also be noted that the above-said methods and compositions are especially useful for the control of terrestrial gastropods such as snails and slugs and aquatic or semi-aquatic mollusks such as cowries and limpets or the snail vectors of schistosomiasis.

DETAILED DESCRIPTION OF THE INVENTION

In accordance with the present invention insects, acarids and mollusks may be controlled by contacting said pests or their food supply with an insecticidally, acaricidally or molluscicidally effective amount of a pyrrole carbonitrile or nitropyrrole depicted by formula I:

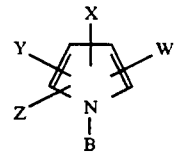 (I)

wherein
W is CN or $NO_2$;
X is CN, Br, Cl, I or $CF_3$;
Y is H, Br, Cl, I or $CF_3$;
Z is H, Br, Cl or I; and
B is

hydrogen,
$C_1$-$C_6$ alkyl optionally substituted with one to three halogen atoms,
one tri($C_1$-$C_4$ alkyl)silyl,
one hydroxy,
one cyano,
one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$c_6$ alkoxycarbonyl group optionally substituted with one to three halogen atoms or one to three $C_1$-$C_4$ alkoxy groups, or
one benzyloxycarbonyl group optionally substituted on the phenyl ring with one to three halogen atoms, one to three $C_1$-$C_4$ alkyl groups or one to three $C_1$-$C_4$ alkoxy groups,
$C_3$-$C_6$ alkenyl optionally substituted with one to three halogen atoms or one phenyl group,
$C_3$-$C_6$ alkynyl optionally substituted with one to three halogen atoms or one phenyl group,
or cyano
R is $C_1$-$C_6$ alkyl optionally substituted with one to three halogen atoms,
one hydroxy,
one cyano,
one or two $C_1$-$C_4$ alkoxy groups optionally substituted with one to three halogen atoms,
one $C_1$-$C_4$ alkylthio, one phenyl optionally substituted with one to
three halogen atoms, one to three $C_1$-$C_4$ alkyl groups or one to three $C_1$-$C_4$ alkoxy groups, one phenoxy group optionally substituted with one to three halogen atoms, one to three $C_1-C_4$ alkyl groups or one to three $C_1-C_4$ alkoxy groups, one benzyloxy group optionally substituted on the phenyl ring with one to three halogen atoms, one to three $C_1-C_4$ alkyl groups or one to three $C_1-C_4$ alkoxy groups, one $C_1-C_6$ alkylcarbonyloxy group optionally substituted with one to three halogen atoms, one $C_2-C_6$ alkenylcarbonyloxy group optionally substituted with one to three halogen atoms, one phenylcarbonyloxy group optionally substituted with one to three halogen atoms, one to three $C_1-C_4$ alkyl groups or one to three $C_1-C_4$ alkoxy groups, $C_1-C_6$ alkoxycarbonyl group optionally substituted with one to three halogen atoms or one to three $C_1-C_4$ alkoxy groups, or one benzyloxycarbonyl group optionally substituted on the phenyl ring with one to three halogen atoms, one to three $C_1-C_4$ alkyl groups or one to three $C_1-C_4$ alkoxy groups, $C_3-C_6$ alkenyl optionally substituted with one to three halogen atoms or one phenyl group, $C_3-C_6$ alkynyl optionally substituted with one to three halogen atoms or one phenyl group, phenyl optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or alkanoylamino, phenoxy optionally substituted with one to three halogen atoms, one or two $C_1-C_4$ alkyl groups, one or two $C_1-C_4$ alkoxy groups, $CF_3$, CN, $NO_2$, di($C_1-C_4$alkyl)amino or alkanoylamino, $C_1-C_6$ alkoxy optionally substituted with one to three halogen atoms, $C_2-C_6$ alkenyloxy optionally substituted with one to three halogen atoms, di($C_1-C_4$alkyl)amino, N-($C_1-C_4$alkyl)-N-phenylamino or -N-halophenylamino, or $C_3-C_6$ polymethyleneimino.

The present invention also relates to novel pyrrole carbonitrile and nitropyrrole compounds having the structure:

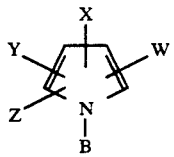

wherein

B, W, X, Y and Z are as described hereinabove for formula I with the proviso that when Y and Z are hydrogen and X is halogen or cyano, B cannot be hydrogen;

when W is $NO_2$ and B is hydrogen and one of Y and Z is hydrogen, then W is attached to one of the pyrrole ring carbon atoms adjacent to the nitrogen;

when W is $NO_2$ and B is hydrogen, then X, Y and Z cannot be chlorine or iodine;

when W is $NO_2$ and X is halogen and Y and Z are hydrogen and W and Y or Z are attached to the pyrrole ring carbon atoms adjacent to nitrogen, then R cannot be methyl;

when W is $NO_2$ and X is CN and Y and Z are hydrogen, then B cannot be methyl, propyl or hydroxyethyl;

when B is hydrogen and X and Y are halogen and Z is hydrogen and W is CN and W is attached to one of the pyrrole ring carbon atoms adjacent to nitrogen, then one of X and Y must be attached adjacent to the carbon atom containing W;

when W and X are CN and Y and Z are Cl and Y and Z are both attached to the pyrrole ring carbon atoms adjacent to nitrogen, then B cannot be hydrogen or methyl; and when W and X are CN and Y and Z are hydrogen, then B cannot be methyl.

Examples of some of the insecticidal, acaricidal and molluscicidal pyrrole carbonitrile and nitropyrrole compounds of the present invention are:

2,4-bis-(Trifluoromethyl)pyrrole-3-carbonitrile;
4-Bromo-1-(hydromethyl)-3,5-bis-(trifluoromethyl)pyrrole-2-carbonitrile, acetate (ester); 2,4,5-Tribromo-1-(hydroxymethyl)pyrrole-3-carbonitrile, p-chlorobenzoate (ester);
2,4,5-Trichloro-2-hydroxymethyl-3-nitropyrrole, pivalate (ester);
2,4,5-Trichloro-1-[1-(2,2,2-trichloroethoxy)ethyl]-pyrrole-3-carbonitrile;
3,4,5-Tribromo-1-(2-chloro-1-ethoxyethyl)pyrrole-2-carbonitrile;
2,5-Dibromo-1-(3,4-dichlorobenzyloxymethyl)pyrrole-3,4-dicarbonitrile;
2,4 5-Tribromo-1-(dimethylcarbamoyl)pyrrole-3-carbonitrile;
3,4-Dichloro-1-[1-(3,4-dimethoxyphenyloxy)ethyl]pyrrole-3-carbonitrile;
2,4,5-Tribromo-1-(3-bromo-4-ethoxybenzoyl)pyrrole-3-carbonitrile;
1-Methyl-2,4,5-tribromopyrrole-3-carbonitrile;
2,4,5-Tribromopyrrole-3-carbonitrile;
1-Cyano-2,4,5-tribromopyrrole-3-carbonitrile;
1-Methyl-2,4,5-trichloropyrrole-3-carbonitrile;
1-(Ethoxymethyl)-2,4,5-tribromopyrrole-3-carbonitrile;
1-Methyl-2,4,5-triiodopyrrole-3-carbonitrile;
4,5-Dibromo-2-(trifluoromethyl)pyrrole-3-carbonitrile;
4,5-Dibromo-1-methyl-2-(trifluoromethyl)pyrrole-3-carbonitrile;
3,4-Dibromo-5-nitropyrrole-2-carbonitrile;
3,5-Dibromo-4-nitropyrrole-2-carbonitrile;
2,4,5-Trichloropyrrole-3-carbonitrile;
4-Nitropyrrole-2-carbonitrile;
1-Methyl-5-nitropyrrole-2-carbonitrile;
2,4,5-Triiodopyrrole-3-carbonitrile;
1-Benzyl-2,4,5-tribromopyrrole-3-carbonitrile;
1-Allyl-2,4,5-tribromopyrrole-3-carbonitrile;
Ethyl 2,4,5-Tribromo-3-cyanopyrrole-1-acetate;
2,4,5-Tribromo-1-ethylpyrrole-3-carbonitrile;
1-Benzyl-2,4,5-trichloropyrrole-3-carbonitrile;
2,4,5-Tribromopyrrole-1,3-dicarbonitrile;
2,4,5-Trichloropyrrole-1,3-dicarbonitrile;
3,4,5-Tribromo-1-methylpyrrole-2-carbonitrile;
3,4,5-Tribromopyrrole-2-carbonitrile;
5-Nitropyrrole-2-carbonitrile;
3,5-Dibromopyrrole-2,4-dicarbonitrile;
3,5-Dibromo-1-methylpyrrole-2,4-dicarbonitrile;
1-Ethoxymethyl-5-nitropyrrole-2-carbonitrile;
1-Methyl-4,5-dibromo-2-(trifluoromethyl)pyrrole-3-carbonitrile;

2-Chloro-4-nitropyrrole;
2,5-Dichloro-3-nitropyrrole;
2,3-Dichloro-4-nitropyrrole;
2,3,5-Trichloro-4-nitropyrrole;
Pyrrole-2,4-dicarbonitrile;
3,4,5-Tribromo-1-(2-propynyl)pyrrole-2-carbonitrile;
2-(Trifluoromethyl)pyrrole-3-carbonitrile;
2,4,5-tribromo-1-(3,4-dichlorobenzoyl)pyrrole-3-carbonitrile
2,4,5-tribromo-1-(2-bromo-4-methoxybenzoyl)pyrrole-3-carbonitrile
2,4,5-tribromo-1-(m-trifluoromethylbenzoyl)pyrrole-3-carbonitrile
p-cyanophenyl 2,3,5-tribromo-4-cyanopyrrole-1-carboxylate
2,6-dichlorophenyl 2,3,5-tribromo-4-cyanopyrrole-1-carboxylate
t-butyl 2,3,5-tribromo-4-cyanopyrrole-1-carboxylate
2,2,2-trichloro-1,1-dimethylethyl 2,3,5-tribromo-4-cyanopyrrole-1-carboxylate
2,2,2-trifluoroethyl 2,3,5-tribromo-4-cyanopyrrole-1-carboxylate
2-chloro-2-propenyl 2,3,5-tribromopyrrole-1-carboxylate
2,4,5-tribromo-1-(2,3-dimethylbutyryl)pyrrole-3-carbonitrile
2,4,5-tribromo-1-(α,α-dimethylphenylacetyl)pyrrole-3-carbonitrile
2,4,5-tribromo-1-(3,3-dimethylacryloyl)pyrrole-3-carbonitrile
N-methyl-N-phenyl-2,3,5-tribromo-4-cyanopyrrole-1-carboxamide.

Since these formula I pyrrole carbonitriles and nitropyrroles are highly effective stomach poisons, they may be applied as feeding deterents to the foliage and stems of crop plants which constitute a food source for insects, acarids and mollusks. Application of the formula I pyrrole is, therefore, generally in the form of a liquid spray which protects the plants against the ravages of feeding insects, acarids and mollusks and kills those pests that attempt to feed on the treated plants.

As stomach poisons, the formula I pyrrole compounds are especially useful for control of terrestrial gastropods since they lend themselves to formulation in baits that can be applied to the habitat of the terrestrial gastropods. This permits control of such pests in an easy manner and eliminates the necessity of preparing, spraying and cleaning the plant spray equipment. Bait formulations are particularly well adapted to use by home gardeners but are equally efficacious when employed for large scale crop treatments by farmers.

The formula I pyrrole carbonitriles and nitropyrroles of this invention can be prepared by several synthetic routes.

For example, formula I halo substituted nitropyrroles, halo substituted pyrrole carbonitriles and halo substituted nitropyrrole carbonitriles can be prepared by halogenation of the appropriate nitropyrrole, pyrrole carbonitrile, pyrrole dicarbonitrile or nitropyrrole carbonitrile illustrated by formula II.

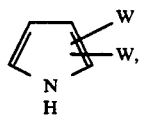

wherein W is CN or NO₂ and W' is hydrogen or CN.

Bromination of a formula II pyrrole is generally achieved by dissolution of the formula II pyrrole in a dilute aqueous base, such as aqueous sodium hydroxide, aqueous potassium hydroxide or the like, and treatment of the thus prepared reaction mixture with at least two to three equivalents of bromine. The reaction may be illustrated as follows:

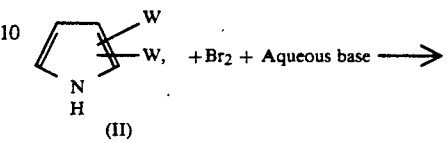

wherein W is CN or NO₂; W' is hydrogen or CN; and n represents the integer 3 when W' is hydrogen and the integer 2 when W' is CN. If desired, the thus prepared brominated nitropyrrole pyrrole mono- or dicarbonitrile or nitropyrrole carbonitrile, can be redissolved in dilute aqueous base and then acidified with a mineral acid such as hydrochloric acid, to obtain the brominated pyrrole or pyrrole carbonitrile in high purify.

It has also been found that bromination of a formula II pyrrole can be achieved by dissolving said formula II pyrrole in an organic solvent such as chloroform, methylene chloride, dioxane, tetrahydrofuran (THF) or the like, and admixing therewith bromine, or N-bromosuccinimide preferably dissolved in the same organic solvent employed for dissolution of the formula II pyrrole. Gentle warming of the reaction mixture may be employed to facilitate the bromination reaction.

Since the above reactions yield a variety of brominated nitropyrroles, brominated pyrrole mono- and dicarbonitriles and brominated nitropyrrole carbonitriles, that are formula I pyrroles by definition, but limited to brominated products, they are identified as group IA products in the reaction illustrated above.

Chlorination of a formula II pyrrole is readily achieved by reaction of the formula II pyrrole with about 2 to 3 equivalents of a chlorinating agent such as chlorine, sulfuryl chloride, or the like, in the presence of an organic acid such as acetic or glacial acetic acid. When sulfuryl chloride is used, the reaction is generally conducted at a temperature below about 40° C. and preferably between 0° C. and 30° C. The reaction may be illustrated as follows:

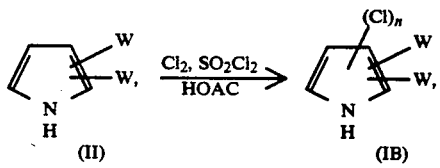

wherein W is CN or NO₂; W' is hydrogen or CN and n represents the integer 3 when W' is hydrogen and integer 2 when W' is CN.

Chlorination of the formula II pyrrole may also be accomplished by reaction of said formula II pyrrole with t-butylhypochlorite or sodium hypochlorite in the presence of an inert organic solvent at reduced temperatures.

The group IB pyrroles, described in the above-reaction, are chlorinated nitropyrroles, chlorinated mono- and dicarbonitriles and chlorinated nitropyrrole carbonitriles, as defined by formula I but are limited to chlorinated products. As such, they are herein identified as group IB products.

Formation of the iodonitropyrroles, the di- and triiodopyrrole carbonitriles or the iodonitropyrrole carbonitriles can be achieved by iodination of an appropriately substituted formula III nitropyrrole carboxylic acid, mono- or dicyanopyrrole carboxylic acid or a cyano and nitro (substituted) pyrrole carboxylic acid dissolved in an aqueous solution of an alkali metal carbonate or bicarbonate. In this reaction the aqueous carbonate solution of the formula II pyrrole is treated with an aqueous solution of iodine and potassium iodide and then heated to a temperature of about 50° C. to 100° C. On cooling, the formula IC iodopyrrole is obtained. The reaction may be illustrated as follows:

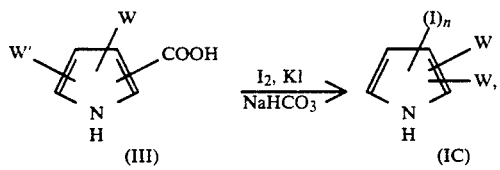

wherein w is CN or $NO_2$; W' is hydrogen or CN; and n is the integer 3 when W' is hydrogen and the integer 2 when W' is CN.

Although the formula IC products, illustrated above, are all encompassed by the definition set forth for formula I, the above reaction provides only iodine substituted nitropyrroles, iodine substituted mono- or dicarbonitriles or iodine substituted nitropyrrole carbonitriles, thus the products of said reaction are designated by formula IC.

Formula I products in which X, Y, and or Y and Z are represented by two different halogen atoms can be prepared by first introducing one or two equivalents of a suitable halogenating agent into a formula II pyrrole followed by separation of the mono- or di-halogenated pyrrole and then adding an additional one or two equivalents of a second halogenating agent to give the formula I tetrasubstituted pyrrole.

Preparation of B-substituted formula I halonitropyrroles, halopyrrole carbonitriles and halonitropyrrole carbonitriles can be achieved by reaction of the appropriately substituted formula I pyrrole having B as hydrogen with an alkylating or acylating agent in the presence of an alkali metal alkoxide or hydride. More particularly, preparation of the B substituted formula I pyrrole involves reaction of formula I pyrrole:

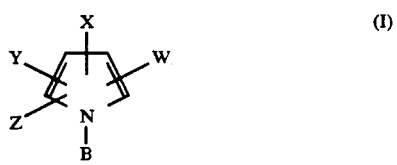

wherein B is hydrogen and W, X, Y and Z are as described in formula I above, with an appropriate alkylating agent such as a $C_1$-$C_6$ alkylhalide in which the alkyl group is straight or branched and is optionally substituted with from one to three halogen atoms, one hydroxy, one cyano, one $C_1$-$C_4$ alkoxy, one $C_1$-$C_4$ alkylthio, one phenyl group, optionally substituted with from one to three halogen atoms, or one benzyloxy group, optionally substituted with from one to three halogen atoms, and an alkali metal alkoxide such as sodium or potassium t-butoxide. This reaction provides a halo nitropyrrole, halopyrrole (mono- or di) carbonitrile or halonitropyrrole carbonitrile having the same substituents as the starting material, but in addition is substituted on the nitrogen with a $C_1$-$C_6$ alkyl group optionally substituted as described above. The reaction may be illustrated as follows:

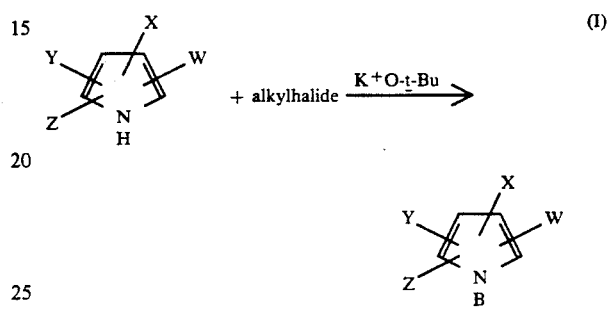

In a similar reaction cyanogen bromide is substituted for the alkylhalide and yields the formula I halo substituted nitropyrrole, halopyrrole carbonitrile or halonitropyrrole carbonitrile having a carbonitrile, rather than an alkyl group, on the nitrogen. Formula IA, IB and IC compounds may also be alkylated in accordance with the above procedure by substituting a compound according to formula IA, IB or IC for the formula I pyrrole in which W, X, Y and Z represent substituents as described above and B is hydrogen.

Advantageously, the above-described alkylation procedure of the formula I, IA, IB and IC, halo (substituted) pyrroles, in which B is hydrogen, may also be applied to the preparation of formula I halopyrroles having an N-$C_3$-$C_6$ alkenyl or N-$C_3$-$C_6$ alkynyl substituent. This N-substitution can be obtained by simply substituting a $C_3$-$C_6$ alkenyl halide or $C_3$-$C_6$ alkynyl halide for the $C_1$-$C_6$ alkyl halide in the above-described reaction.

In a similar manner, preparation of N-acylated halonitropyrroles, halopyrrole carbonitriles and halonitro pyrrole carbonitriles can be achieved by the reaction of an appropriately substituted formula I pyrrole wherein B is hydrogen with an acylating agent in the presence of an alkalai metal alkoxide. Acylating agents such as $C_1$-$C_6$ alkyl or $C_2$-$C_6$ alkenyl acid chloride, substituted $C_1$-$C_6$ alkly or $C_2$-$C_6$ alkenyl acid chloride, benzoyl chloride, substituted benzoyl chloride, phenylchloroformate, substituted phenylchloroformate, $C_1$-$C_6$ alkyl or $C_2$-$C_6$ alkenylchloroformate, substituted $C_1$-$C_6$ alkyl or $C_2$-$C_6$ alkenylchloroformate, N-substituted carbamoyl chloride and the like may be employed. The reaction may be illustrated as follows:

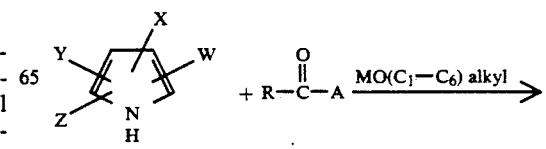

-continued

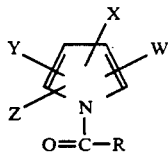

wherein A is halogen, M is alkalai metal and W, X, Y, Z and R are as described hereinabove for formula I.

Preparation of (trifluoromethyl)pyrrole carbonitriles and conversion thereof to dihalo (trifluoromethyl)pyrrole carbonitriles and dihalo- alkylated N-(trifluoromethyl)pyrrole carbonitriles can be achieved by the admixture of a dispersion of sodium hydride in tetrahydrofuran with a solution of ethyl trifluoroacetate and 3-cyano propionaldehyde diethyl acetal in tetrahydrofuran. The reaction that occurs yields 3-trifluoroacetyl-3-cyanopropionaldehyde diethyl acetal which is then heated with oxalic acid dihydrate in water to give the 3-trifluoroacetyl-3-cyanopropionaldehyde. The thus prepared aldehyde is then dissolved in glacial acetic acid and the resulting solution treated with ammonium acetate to provide the 2-(trifluoromethyl)pyrrole-3-carbonitrile. Halogenation of the above-said (trifluoromethyl)pyrrole carbonitrile may then be accomplished by reaction of said (trifluoromethyl)pyrrole carbonitrile with N-bromosuccinimide or N-chlorosuccinimide in the presence of tetrahydrofuran to yield the dihalo (trifluoromethyl)pyrrole carbonitrile. Alkylation or acylation of this dihalo (trifluoromethyl)pyrrole carbonitrile with an alkyl halide or acylhalide in the presence of potassium t-butoxide and tetrahydrofuran yields the N-alkylated (or N-acylated) dihalo (trifluoromethyl)pyrrole carbonitrile.

Other methods for the preparation of the formula I halo substituted nitropyrroles, halo substituted pyrrole carbonitriles, halo substituted nitropyrrole carbonitriles and the N-substituted derivatives thereof, will become apparent from the examples set forth below.

The formula I pyrroles of this invention, which include halo substituted nitropyrroles, halo substituted pyrrole carbonitriles, halo substituted nitropyrrole carbonitriles and the N-substituted derivatives thereof, are effective for controlling insects, acarine and mollusks, particularly mollusks of the class gastropoda, which includes snails, slugs, cowries and limpets. These compounds are also effective for protecting growing and harvested plants and crops from attack by the above-said pests.

To achieve such control or plant protection, a water or liquid spray containing from about 10 ppm to 10,000 ppm and preferably about 100 to 5000 ppm of a formula I pyrrole carbonitrile or nitropyrrole, applied to plants, crops or the soil or water in which said plants or crops are growing, is effective for protecting them from attack by said insects, acarina or gastropoda. These compositions are likewise effective for protecting turf grass from attack by pests such as grubs, chinch bugs and the like. Effective spray applications for the protection of plants, crops, turf and the like, usually provide about 0.125 kg/ha to 4.0 kg/ha of the active pyrrole, although higher rates of application of the formula I pyrroles may be used if desired.

It is also found that the formula I pyrroles are effective for the protection of plants and crops when applied to the foliage of said plants and/or the habitat in which said plants are growing, as a dust, dust concentrate, bait or other solid formulation which provides about 0.125 kg/ha to 4.0 g/ha of the active pyrrole to the locus of treatment. Higher rates of pyrrole application in solid formulations may also be used, but usually are not required for plant protection against the pests described.

It has been further determined that an especially effective method for controlling terrestrial gastropods with the formula I pyrroles of the invention, is to proffer the active molluscicidal material in the form of a bait formulation. These bait formulations can be widely varied but generally contain about 1% to 20% by weight and preferably about 5% to 10% by weight of the active ingredient, about 40% to 50% by weight of a solid edible nutritive substance, about 5% to 10% by weight of a carbohydrate source such as sugar, molasses, corn syrup or the like and the remainder of the formulation, i.e. about 30% to 50% by weight of water or other consumable liquid.

A preferred bait formulation will contain about 5% by weight of the pyrrole dispersed in a bait comprising about 46% of unprocessed bran, 6% by weight of molasses and 48% by weight of water.

In addition to bait formulations, the above-said pyrroles may be formulated into dry compacted granules, flowable compositions, granular formulations, wettable powders, dusts, dust concentrates, microemulsions, emulsifiable concentrates and the like, all of which lend themselves to soil, water and/or foliage application and provide the requisite plant protection. Such formulations include the compounds of the invention admixed with inert, pharmacologically-acceptable solid or liquid diluents.

Typical wettable powder, dust and dust concentrate formulations of the invention can be prepared by grinding together about 3% to 20%, by weight, of the formula I pyrrole compound, with about 3% to 20% by weight of a solid anionic surfactant. One suitable anionic surfactant is a dioctyl ester of sodium sulfosuccinic acid, specifically Aerosol OTB ® surfactant marketed by the American Cyanamid Company. About 60% to 94%, by weight, of an inert solid diluent, such as montmorillonite, attapulgite, chalk, talc, kaolin, diatomaceous earth, limestone, silicates or the like, also is used in such formulations.

Compacted granules especially useful for soil or water application can be prepared by grinding together in about equal parts, usually about 3 to 20 parts, of the pyrrole and a solid surfactant, with about 60 to 94 parts of gypsum. Thereafter, the mixture is compacted into small granular particles, generally about 24/48 mesh or larger.

Other suitable solid surfactants useful in the present formulations include a variety of conventional anionic surfactants as well as nonionic block copolymers of ethylene oxide and propylene oxide. A number of said block copolymers that can be used with the pyrroles of the present invention are marketed by BASF Wyandotte Corporation as Pluronic 10R8 ®, 17R8 ®, 25R8 ®, F38 ®, F68 ®, F77 ® or F87 ®. The later surfactants are especially effective for the preparation of compacted granules.

While the pyrroles of the invention are effective for controlling insects, mollusks and acarina when employed alone, they may also be used in combination with other biocidal chemicals, including other insecticides, molluscicides and acaricides. For example, the pyrroles of this invention may be used effectively in conjunction or combination with phosphates, carbamates, pyrethroids, formamidines, chlorinated hydrocarbons, halobenzoylureas and the like, including bacterial and viral insecticides.

Where solid formulations of the compounds of this invention are to be employed in combination treatments with other pesticidal agents, the formulations can be applied as an admixture of the components or may be applied sequentially.

Similarly, liquid formulations of the pyrrole in combination with other pesticidal agents may be tank mixed or may be applied separately, sequentially, as liquid sprays.

The following examples are presented as illustrations of the present invention and the invention is not to be limited thereby.

EXAMPLE 1

Preparation of 1-Methyl-5-nitropyrrole-2-carbonitrile

To a solution of 300 mg of 5-nitropyrrole-2-carbonitrile (2.14 mmol) in 15 mL of acetone, 360 mg of potassium carbonate (2.6 mmol) and 0.165 mL of iodomethane (1.6 mmol, 372 mg) are added. The mixture is then stirred at room temperature for 24 hours. The reaction mixture is poured into ice-water (100 mL) and the precipitate which forms is collected to yield (200 mg), 62%; mp 86°–87° C. of 1-methyl-5-nitropyrrole-2-carbonitrile.

EXAMPLE 2

Preparation of 1-Ethoxymethyl-5-nitropyrrole-2-carbonitrile

To a solution of 560 mg of 5-nitropyrrole-2-carbonitrile (4 mmol) in 20 mL of dry THF, is added 515 mg of potassium tert-butoxide (4.6 mmol). After the addition of 0.45 mL of chloromethylethylether (4.8 mmol) to the mixture, the mixture is stirred for 4 hours, then diluted with ether (30 mL) and water (50 mL). The organic layer is separated, washed with water MgSO$_4$ (20 mL) and dried over MgSO$_4$. After evaporation of the solvent a red oil is obtained (600 mg, 75%) 1-(ethoxymethyl)-5-nitropyrrole-2-carbonitrile.

Anal. Calcd: C, 49.23%; H, 4.65%; N, 21.53%.
Found: C, 49.40%; H, 4.07%; N, 21.30%.

EXAMPLE 3

Preparation of 3-Trifluoroactyl-3-cyanopropionaldehyde diethyl acetal

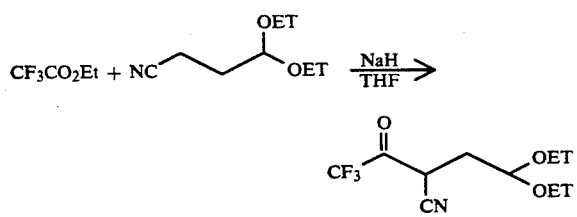

To a 40°–45° C. stirring suspension of hexane-washed sodium hydride (5.5 g of a 60% dispersion, 0.14 mol) in 200 mL of dried tetrahydrofuran is added dropwise a solution of ethyl trifluoroacetate (15 g, 0.11 mol) and 3-cyanopropionaldehyde diethyl acetal (17 g, 0.11 mol) in 100 mL of dry tetrahydrofuran. The previously gray suspension slowly turns light brown in color. The reaction mixture is stirred at 50°–55° C. overnight before being quenched by slow addition of 2-propanol (15 mL). Rotary evaporation of the volatiles yields a dark oil, to which is added 150 mL of pH 7 water. Unreacted starting materials are conveniently removed by washing the aqueous layer with diethyl ether (3×30 mL). The basic aqueous phase is then acidified with 12 N hydrochloric acid and extracted with ethyl acetate (2×100 mL). The combined organic layers are washed once with saturated sodium bicarbonate (40 mL) and once with brine (15 mL) before being dried over magnesium sulfate. Rotary evaporation yields a reddish oil which is flash chromatographed over silica gel using 4:1 hexane-ethyl acetate as eluent to provide the desired product (9 g, 32%) as a yellow oil.

EXAMPLE 4

Preparation of 3-Trifluoroacetyl-3-cyanopropionaldehyde

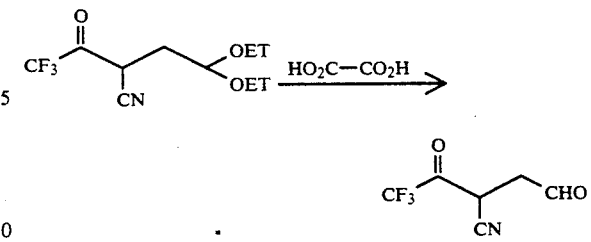

A mixture of the 2-trifluoroacetylcyanopropionaldehyde-4,4-diethyl acetal (5.0 g, 0.02 mol) and oxalic acid dihydrate (1.2 g, 0.01 mol) in 75 mL of water is heated to reflux for 20 minutes. After the reaction is allowed to cool, sodium bicarbonate (1.7 g, 0.02 mol) is added followed by 100 mL of ethyl acetate. The layers are separated and the organic phase is washed once with brine (15 mL) before being dried over magnesium sulfate. Rotary evaporation yields a dark oil which is used immediately in the next step of the reaction sequence.

EXAMPLE 5

Preparation of 2-(Trifluoromethyl)pyrrole-3-carbonitrile

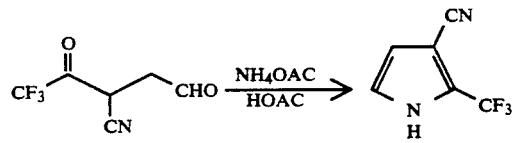

The crude aldehyde (isolated from the previous step (4.5 g) is dissolved in 50 mL of glacial acetic acid, followed by ammonium acetate (1.5 g, 0.02 mol). The mixture is heated to 65°–70° C. for one hour, allowed to cool, and is then poured into 100 mL of water. Extraction with ethyl acetate (2×75 mL) is followed by bicarbonate washing of the combined organic phases until no acid remains. The red solution is then dried over magnesium sulfate and rotary evaporated to a dark oil. Purification over silica gel using 4:1 hexane-ethyl acetate as eluent affords the 2-trifluoromethyl-3-cyanopyrrole (0.7 g, 4.3 mmol, 22% from the acetal) as a light yellow solid, mp 122°–124° C.

EXAMPLE 6

Preparation of 1-(ethoxymethyl)-2-(trifluoromethyl)pyrrole-3-carbonitrile

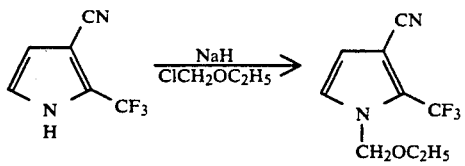

A stirred solution of 2-trifluoromethyl-3-cyanopyrrole (1.0 g, 6.2 mmol) in dry tetrahydrofuran is treated with NaH (0.30 g, 7.5 mmol) as a 60% dispersion in mineral oil, under nitrogen, at room temperature. After 20 minutes, the reaction mixture is treated dropwise with a solution of chloromethyl ethyl ether (0.77 g, 8.1 mmol) in dry tetrahydrofuran, stirred vigorously for 3 hours and treated with a mixture of 1N HCl and ethyl acetate. The phases are separated and the organic phase is washed with brine, dried over Mg SO₄ and concentrated in vacuo to afford a residue. Flash chromatography of the residue using silica gel and 3.5:1 hexane:ethyl acetate yields the title compound as a pale yellow oil, 0.83 g (61%).

EXAMPLE 7

Preparation of 4,5-Dibromo-2-(trifluoromethyl)pyrrole-3-carbonitrile

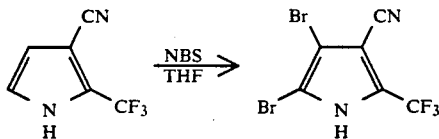

To a solution of 2-(trifluoromethyl)pyrrole-3-carbonitrile (1.0 g, 6.2 mmol) in 40 mL of tetrahydrofuran is added N-bromosuccinimide (2.2 g, 13 mmol) portionwise. The reaction mixture is allowed to stir overnight at room temperature before being quenched with saturated aqueous sodium thiosulfate (5 mL). Water (15 mL) and diethyl ether (50 mL) are added and the layers separated. The organic layer is washed with brine (10 mL) and dried over magnesium sulfate. Rotary evaporation yields a crude solid which is flash chromatographed using 2:1 hexane-ethyl acetate doped with acetic acid (2 mL per 300 mL of solvent) as eluent. The desired 2-trifluoromethyl-3-cyano-4,5-dibromopyrrole (0.8 g, 2.5 mmol, 40%) is isolated as a pale yellow solid.

EXAMPLE 8

Preparation of 4,5-Dibromo-1-methyl-2-(trifluoromethyl)pyrrole-3-carbonitrile

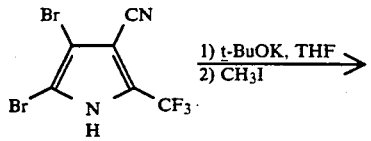

-continued

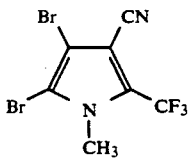

To a solution of the 2-trifluoromethyl-3-cyano-4,5-dibromopyrrole (0.5 g, 1.6 mmol) in 30 mL of dry tetrahydrofuran is added potassium tert-butoxide (0.2 g, 1.9 mmol) portionwise. The rose colored solution is allowed to stir for 20 minutes before the addition of methyl iodide (0.6 g, 4.2 mmol) neat. The resulting suspension is stirred for 5 hours before being quenched by the addition of 10 mL of water. Diethyl ether (50 mL) is also added and the layers are separated. The organic phase is washed with brine (10 mL) and dried over magnesium sulfate. Rotary evaporation yields a crude solid which is flash chromatographed over silica gel using 4:1 hexane-ethyl acetate as eluent to provide the N-methylated pyrrole (0.4 g, 1.2 mmol, 77%) as a light yellow solid, mp 123°–125° C.

Using the same procedure and substituting chloromethyl ethyl ether as the alkylating agent affords 4,5-dibromo-1-(ethoxymethyl)-2-(trifluoromethyl)pyrrole-3-carbonitrile as a white solid, mp 65°–67° C.

EXAMPLE 9

Preparation of 3,4-Dibromo-5-nitropyrrole-2-carbonitrile

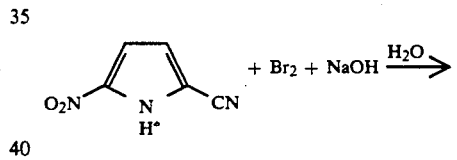

A sample of 5-nitropyrrole-2-carbonitrile 0.4 g, 0.003) is readily soluble in 10 mL of dilute sodium hydroxide (0.4 g, 0.01 mol). Bromine (0.96 g, 0.006 mol) is added dropwise which results in the deposition of a solid precipitate. Additional 10% sodium hydroxide is added until all the solid is dissolved. The solution is then stirred 15 minutes before acidifying with dilute hydrochloric acid. The white precipitate is collected and dried. The product (0.5 g, 56%) has mp 181°–186° C.

EXAMPLE 10

Preparation of 3,5-Dibromo-4-nitropyrrole-2-carbonitrile

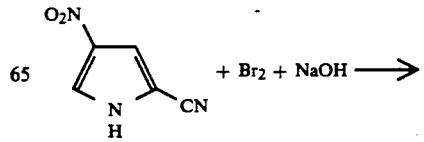

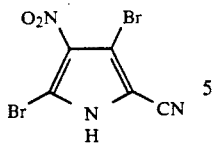

4-Nitropyrrole-2-carbonitrile (0.6 g, 0.0042 mol) is readily soluble in 15 mL of water containing sodium hydroxide (0.5 g, 0.012 mol). Bromine (1.34 g, 0.008 mol) is added dropwise, resulting in the formation of a solid precipitate. Sodium hydroxide (10% solution) is then added until the solid is dissolved. The resulting solution is stirred for 15 minutes before acidifying the solution with dilute hydrochloric acid. The white precipitate (1.0 g, 83%) has mp 170°–175° C.

Calcd. for $C_5HBr_2N_3O_2$: C, 20.35; H, 0.33; N, 14.24; Br, 54.20.

Found: C, 20.72; H, 0.23; N, 14.16; Br, 53.50.

EXAMPLE 11

Preparation of 2,4,5-Trichloropyrrole-3-carbonitrile

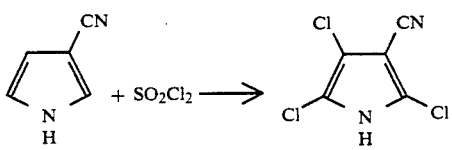

To a stirred mixture of 1.50 g (16.3 mmol) of pyrrole-3-carbonitrile in 50 mL of glacial acetic acid is added quickly dropwise 4.1 mL (51.0 mmol) of sulfuryl chloride by syringe through a rubber septum. With this addition the temperature of the reaction mixture rises from about 22° C. to 32° C. The mixture is stirred one and one-half hours and then diluted with carbonitrile in 20 mL of dry THF over a 15 minute period. After 15 minutes, 0.50 mL (8.03 mmol) of methyl iodide is added dropwise by syringe over 10 minutes. Solids are formed and after stirring for about 3 hours, the mixture is diluted with 100 mL of water. The cloudy mixture is extracted twice with ethyl acetate and the combined organic layers washed successively with dilute NaOH, water, and saturated salt solution. After drying over magnesium sulfate, the organic mixture is filtered and concentrated in vacuo to give 0.99 g of an off-white solid. Purification by chromatography on silica gel using methylene chloride affords 0.68 g of yellow-white solid which is slurried with hexane and recovered by filtration; mp 110°–114° C.

Anal. Calcd for $C_6H_3Cl_3N_2$: C, 34.40; H, 1.44; N, 13 38; Cl, 50.78.

Found: C, 34.25; H, 1.50; N, 13.36; Cl, 50.88.

EXAMPLE 15

Preparation of 1-Methyl-2,4,5-tribromopyrrole-3-carbonitrile

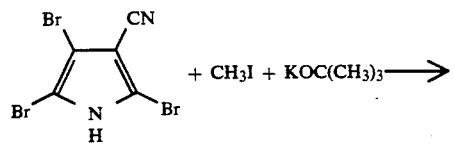

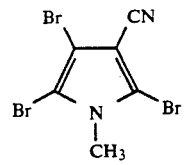

To a stirred mixture of 0.87 g (7.75 mmol) of potassium t-butoxide in 30 mL of dry THF under a nitrogen atmosphere is added dropwise from an addition funnel 2.10 g (6.39 mmol) of 2,4,5-tribromopyrrole-3-carbonitrile in 20 mL of dry THF. After 15 minutes, 0.64 mL (10.3 mmol) of methyl iodide is added by syringe over 2 minutes. After several hours at room temperature, the mixture is diluted with 100 mL of water and 75 mL of ethyl acetate. The separated water

EXAMPLE 13

Preparation of 2,4,5-Triiodopyrrole-3-carbonitrile

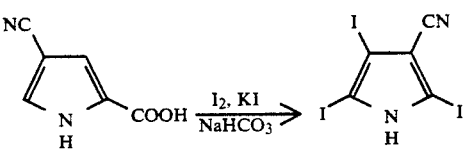

4-Cyanopyrrole-2-carboxylic acid (1.36 g, 0.01 mol) is added to a warm suspension of sodium bicarbonate (16.8 g, 0.2 mol) in water (150 mL). After all the acid has dissolved, a solution of iodine (8.3 g, 0.033 mol) and potassium iodide (11.0 g, 0.066 mol) in water (50 mL) is slowly added with stirring over 1 hour. The mixture is heated at 70°–80° C. for 2 hours and cooled in an ice bath and then left in the refrigerator overnight. The solids are collected, washed well with water and are dried. Flash column chromatography on silica gel packed in methylene chloride and eluted with.3% ethyl acetate in methylene chloride gives the product as a yellow solid on crystallization from ethyl acetate (0.65 g); mp 257.0°–258.0° C.

EXAMPLE 14

Preparation of 1-Methyl-2,4,5-trichloropyrrole-3-carbonitrile

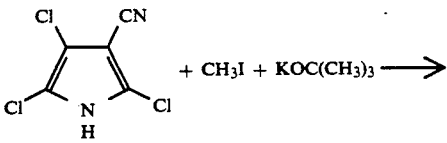

To a stirred mixture of 0.70 g (6.2 mmol) of potassium t-butoxide in 25 mL of dry THF under a nitrogen atmosphere, is added dropwise from an addition funnel 1.00 g (5.12 mmol) of 2,4,5-trichloropyrrole-3-100 mL of water. The resulting solids are collected by filtration and washed with water. On drying, the yield is 2.23 g (70%) of white solid, mp >300° C.

EXAMPLE 12

Preparation of 2,4,5-Tribromopyrrole-3-carbonitrile

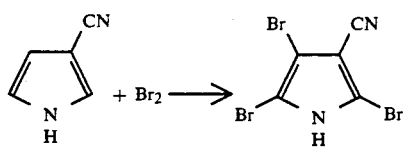

To a stirred mixture of 1.50 g (16.3 mmol) of pyrrole-3-carbonitrile in 20 mL of chloroform is added dropwise from an addition funnel a mixture of 2.5 mL (48.5 mmol) of bromine in 7.5 mL of chloroform over about 30 minutes. The temperature of the mixture rises to 38° C. and a gummy solid is formed which necessitates addition of additional chloroform (25 mL) and some warming to achieve good stirring. The mixture is stirred an additional 2 hours at room temperature and the solid product is collected by filtration and washed with chloroform. The collected solids amount to 4.55 g. Concentration of the filtrate affords another 0.58 g of product. The combined solids are slurried with boiling methylene chloride. On cooling, filtration gives 3.66 g of a pale orange powder, mp 253°-255° C.

Anal. Calcd for $C_5HBr_3N_2$: C, 18.26; H, 0.31; N, 8.52; Br, 72.91

Found: C, 18.28; H, 0.35; N, 8.52; Br, 72.74. phase is extracted again with ethyl acetate and the combined organic layers are washed with dilute sodium hydroxide, water, and saturated salt solution. After drying over magnesium sulfate, the mixture is shaken with activated charcoal and filtered. Concentration in vacuo gives a white solid which is slurried with hexane and recrystallized from ethyl acetate to afford the title compound as a white solid, mp 151°-152° C.

Using the same procedure and employing 4,5-dibromopyrrole-3-carbonitrile as substrate affords 1-methyl-4,5-dibromopyrrole-3-carbonitrile as a white solid, mp 138°-139° C.

EXAMPLE 16

Preparation of 1-Benzyl-2,4,5-tribromopyrrole-3-carbonitrile

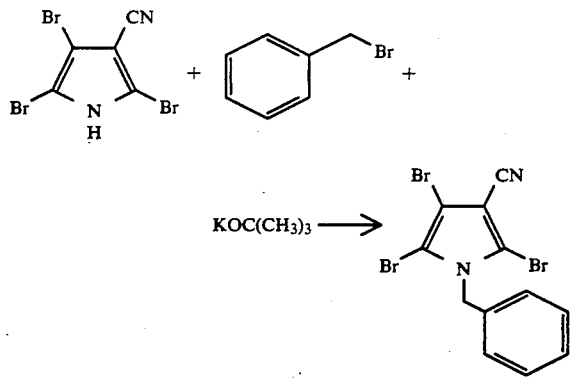

To a stirred mixture of 1.00 g (3.04 mmol) of 2,4,5-tribromopyrrole-3-carbonitrile and 0.68 g (6.1 mmol) of potassium t-butoxide in 30 mL of dry THF under a nitrogen atmosphere is added 1.10 mL of benzyl bromide. The mixture is heated to reflux and stirred overnight. After dilution with 100 mL of water and 150 mL of ethyl acetate, the organic mixture is separated and washed with salt solution, dried over magnesium sulfate, and concentrated in vacuo to leave 2.34 g of orange oil. The oil is triturated under a mixture of 5:1 hexane/ether to give a white solid collected by filtration; 0.81 g, mp 100°-103° C. The filtrate yields a second crop; 0.11 g, mp 100°-103° C.

EXAMPLE 17

Preparation of 1-Allyl-2,4,5-tribromopyrrole-3-carbonitrile

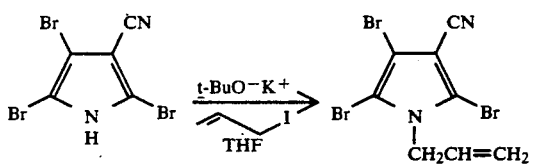

Potassium t-butoxide (0.75 g, 6.7 mmol) is added portionwise at room temperature to a solution of 2,4,5-tribromopyrrole-3-carbonitrile (2.0 g, 6.1 mmol) in anhydrous tetrafuran (20 mL). After 30 minutes allyl iodide (1.12 g, 6.7 mmol) is added dropwise and then refluxed for 2 hours. Work-up as described in Example 15 gives the product as a pale pink liquid (2.1 g).

EXAMPLE 18

Preparation of Ethyl 2,4,5-Tribromo-3-cyanopyrrole-1-acetate

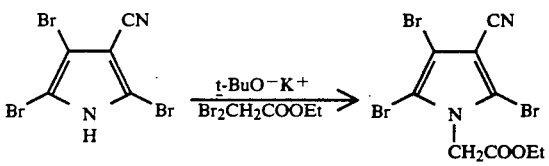

Potassium t-butoxide (0.75 g, 6.7 mmol) is added in portions at room temperature to a solution of 2,4,5-tribromopyrrole-3-carbonitrile (2.0 g, 6.1 mmol) in anhydrous tetrahydrofuran (20 mL). After 30 minutes, ethyl bromoacetate (1.12 g, 6.7 mmol) is added dropwise and the mixture stirred for 4-5 hours at room temperature. Work-up as described in Example 15 gives the product as white solid (0.42 g); m; 140°-143° C.

EXAMPLE 19

Preparation of 2,4,5-Tribromo-1-ethylpyrrole-3-carbonitrile

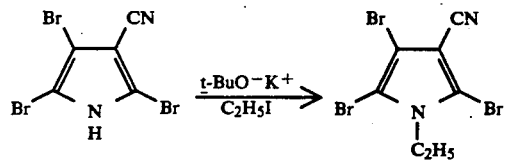

Potassium t-butoxide (0.75 g, 6.7 mmol) is added in portions at room temperature to a solution of 2,4,5-tribromopyrrole-3-carbonitrile (2.0 g, 6.1 mmol) in anhydrous tetrahydrofuran (20 mL). After 30 minutes, ethyl iodide (1.04 g, 6.7 mmol) is added dropwise. The reaction solution is stirred at room temperature for 30 minutes and then refluxed for 90 minutes. The mixture is cooled, diluted with water and extracted with ethyl acetate. The organic layer is washed with water and saturated sodium chloride and dried (Na$_2$SO$_4$). Evaporation of the solvent and crystallization from ether-hexanes gives a solid which is further purified by flash column chromatography on silica gel, packed with methylene chloride and eluted with 3% ethyl acetate in methylene chloride. The analytically pure sample is finally crystallized from methylene chloride-hexanes as a white solid (1.55 g); mp 108.5°–109.5° C.

EXAMPLE 20

Preparation of 2,4,5-Tribromo-1-(substituted)pyrrole-3-carbonitrile

In the same manner described for the preparation of 2,4,5-tribromo-1-ethylpyrrole-3-carbonitrile in Example 19, using the requisite cyanotrihalopyrrole and appropriate alkylating agent, the additional analogs illustrated below are prepared:

| X | Y | Z | B | mp °C. |
|---|---|---|---|---|
| I | I | I | CH$_3$ | 211–214 |
| Cl | Cl | Cl | CH$_2$C$_6$H$_5$ | 87–91 |
| Br | Br | Br | CH$_2$C≡CH | 113–117 |
| Br | Br | Br | CH$_2$OC$_2$H$_5$ | 144–147 |
| Br | Br | Br | CH$_2$CN | 136–138 |
| Br | Br | Br | CH(CH$_3$)OCH$_3$ | 169–171 |
| Br | Br | Br | CH$_2$OCOC(CH$_3$)$_3$ | 69–71 |
| Br | Br | Br | CH$_2$COOC(CH$_3$)$_3$ | 124–126 |
| Br | Br | Br | CH$_2$—C$_6$H$_4$Cl-p | 135–140 |
| Br | Br | Br | CH$_2$—C$_6$H$_3$Cl$_2$-2,4 | 151–154 |
| Br | Br | Br | CH(CH$_2$Cl)OC$_2$H$_5$ | 106–108 |
| Br | Br | Br | CH$_2$OCOCH$_3$ | 136–137 |
| Br | Br | Br | CH$_2$Si(CH$_3$)$_3$ | 110–111 |

EXAMPLE 21

Preparation of 2,4,5-Tribromopyrrole-1,3-dicarbonitrile

Potassium t-butoxide (614 mg, 5.74 mmol) is added in portions at room temperature to a solution of 2,4,5-tribromopyrrole-3-carbonitrile (1.50 g, 4.56 mmol) in anhydrous tetrahydrofuran (20 mL). After 15 minutes a solution of cyanogen bromide (177 mg, 5.74 mmol) in tetrahydrofuran (5 mL) is added dropwise. The reaction solution is stirred at room temperature overnight as it turns cloudy. The mixture is diluted with water and extracted with ethyl acetate. The organic layer is washed with water and saturated sodium chloride and dried over (Na$_2$SO$_4$). Evaporation of the solvent and crystallization of the residue from ether gives a white solid (1.20 g); mp 195.0°–197.5° C.

EXAMPLE 22

Preparation of 3,4,5-Tribromopyrrole-2-carbonitrile

Sodium hydroxide (3.2 g, 0.08 mol) is dissolved in 100 mL of water followed by the addition of pyrrole-2-carbonitrile (2.6 g, 0.027 mol). A few mL of dioxane is added to make the mixture homogenous. Then bromine (12.96 g, 0.081 mol) is added in small portions at 28°–35° C. with periodic cooling. Before the addition is complete, solids begin to precipitate. Everything is brought back into solution by the addition of 10% sodium hydroxide. Then the remaining bromine is added and the solution stirred for 15 minutes before acidifying with dilute hydrochloric acid. The white solid (7.4 g, 84%) is collected and, after drying, has mp 215°–218° C.

. Calcd for C$_5$HN$_2$Br$_3$: C, 18 25; H, 0.30; N, 8.51; Br, 72.92.

Found: C, 18.06; H, 0.37; N, 8.39; Br, 72.72.

EXAMPLE 23

Preparation of 3,4,5-Tribromo-1-methyl-pyrrole-2-carbonitrile

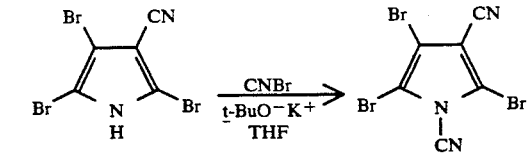

3,4,5-Tribromo-pyrrole-2-carbonitrile (1.0 g, 0.003 mol) is dissolved in a mixture of acetone and dimethoxyethane. Potassium carbonate (0.45 g, 0.0033 mol) is added followed by methyl iodide (0.478 g, 0.0033 mol). After stirring overnight at room temperature, the reaction mixture is poured into water and filtered. The filter cake is air dried to give the title compound as a white solid, 0.8 g (80%), mp 115°–119° C.

Using the same procedure and substituting propargyl bromide as the alkylating agent affords 3,4,5-tribromo-1-(2-propynyl)pyrrole-2-carbonitrile as a yellow solid, mp 95°–105° C.

EXAMPLE 24

Preparation of 3,5-Dibromo-pyrrole-2,4-dicarbonitrile

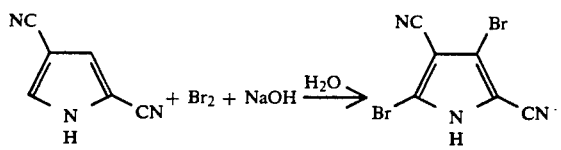

Pyrrole-2,4-dicarbonitrile (0.5 g, 0.004 mol) is readily soluble in 15 mL of water containing sodium hydroxide (0.5 g, 0.012 mol). Bromine (1.34 g, 0.008 mol) is then added and the solution stirred for 15 minutes. Thin layer chromatography (90/10 methylene chloride/acetonitrile) indicates the reaction is incomplete. Additional bromine is added and the reaction monitored by Tlc. When the reaction is complete, the mixture is acidified and a white solid collected. The solid (0.47 g, 40.8%) after recrystallization from dichloroethane (30 mL) has mp 227°-232° C.

Calcd for $C_6HBr_2N_3$: C, 26.20; H, 0.36; N, 15.28; Br, 58.15.

Found: C, 26.25; H, 0.58; N, 15.17; Br, 58.35.

EXAMPLE 25

Preparation of 3,5-Dibromo-1-methylpyrrole-2,4-dicarbonitrile

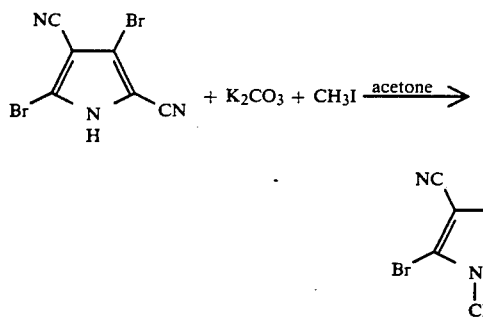

A sample (1.0 g, 0.0036 mol) of 3,5-dibromopyrrole-2,4-dicarbonitrile is readily soluble in 20 mL of acetone. Anhydrous potassium carbonate (0.64 g, 0.0046 mol) is added, and while the slurry is stirred, methyl iodide (0.68 g, 0.0047 mol) is added. The reaction can be followed by Tlc. When the reaction is complete, the mixture is poured into water precipitating a white solid. The product (0.77 g, 74%) has mp 175°-178° C.

Calcd for $C_7H_3Br_2N_3$: C, 29.08; H, 1.04; N, 14.54; Br, 55.33.

Found: C, 29.09; H, 1.42; N, 14.48; 8r, 54.95.

EXAMPLE 26

Preparation of 3-Bromo-2,5-dichloro-4-nitropyrrole

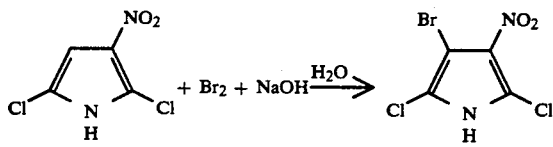

The title compound can be prepared by dissolving a sample of 2,5-dichloro-3-nitropyrrole (0.54 g, 0.003 mol) in 10 mL of dilute sodium hydroxide (0.25, 0.006), and adding bromine (0.48 g, 0.003 mol). If solid precipitates before all the bromine is added, additional base can be added. When the addition is complete, the solution can be acidified with dilute hydrochloric acid to precipitate the desired product.

EXAMPLE 27

Preparation of 4-(trifluoromethyl)pyrrole-3-carbonitrile

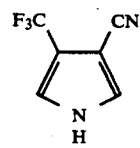

A mixture of p-tolylsulfonylmethylisocyanide (0.72 g, 3.2 mmol) and sodium hydride (0.09 g, 3.8 mmol) in anhydrous ethyl ether is treated dropwise with a solution of 4,4,4-trifluorocrotonitrile (0.38 g, 3.2 mmol) in ether and dimethyl sulfoxide over a 35 minute period, stirred at room temperature for 20 minutes and quenched with water. The phases are separated and the aqueous phase is extracted with ether. The organic phases are combined, washed with brine, dried over $MgSO_4$ and concentrated in vacuo to afford an orange solid residue. The residue is flash chromatographed using silica gel and 100:100:1 petroleum ether: ethyl ether: acetic acid followed by 100% methylene chloride to give the title product as a white solid, mp 96°-97° C.

EXAMPLE 28

Preparation of 2,5-dibromo-4-(trifluoromethyl)pyrrole-3-carbonitrile

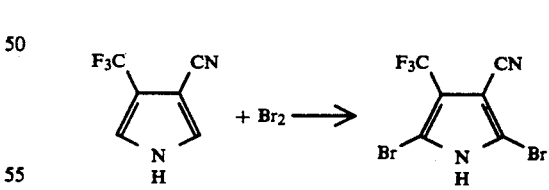

A mixture of 4-(trifluoromethyl)pyrrole-3-carbonitrile (0.10 g, 0.63 mmol) and sodium acetate (0.2 g, 2.4 mmol) in acetic acid is treated dropwise with a solution of bromine (0.23 g, 1.4 mmol) in acetic acid, stirred for 6 hours at 25° C. and poured into an aqueous metabisulfite solution. The resultant mixture is filtered and the filter cake is washed with water and air-dried to yield the title compound as a white solid, 0.11 g (58%), mp 198°-200° C.

EXAMPLE 29

Preparation of 2,5-dibromo-1-methyl-4-(trifluoromethyl)pyrrole-3-carbonitrile

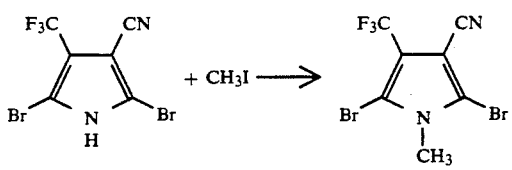

A solution of 2,5-dibromo-4-(trifluoromethyl)pyrrole-3-carbonitrile (0.10 g, 0.30 mmol) in tetrahydrofuran is treated with solid potassium t-butoxide (0.053 g, 0.49 mmol), stirred for 1 hour at 25° C., treated dropwise with methyl iodide (0.067 g, 0.47 mmol), stirred for 2 hours at 25° C. and for 1 hour at 50° C. and diluted with water and ether. The phases are separated and the organic phase is washed sequentially with water and brine, dried over MgSO4 and concentrated in vacuo to afford the title compound as a white solid, 0.09 g, mp 101°-104° C.

EXAMPLE 30

Preparation of 4,5-dibromo-1-methylpyrrole-2-carbonitrile

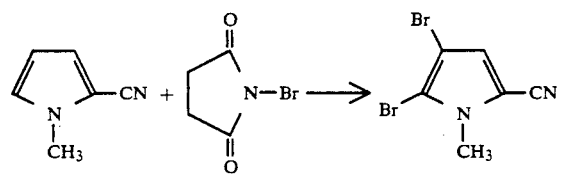

A solution of 1-methylpyrrole-2-carbonitrile (1.06 g, 0.01 mol) in tetrahydrofuran is treated with N-bromosuccinimide (5.34 g, 0.03 mol) at 25°-30° C., stirred for 18 hours at 25° C. and concentrated in vacuo to give a residue. The residue is taken up in carbon tetrachloride, filtered and the filtrate is concentrated in vacuo to give a solid residue. Recrystallization from ethanol/water yields the title product as a grey solid, mp 104°-105° C.

EXAMPLE 31

Preparation of ethyl 4-(trifluoromethyl)pyrrole-3-carboxylate

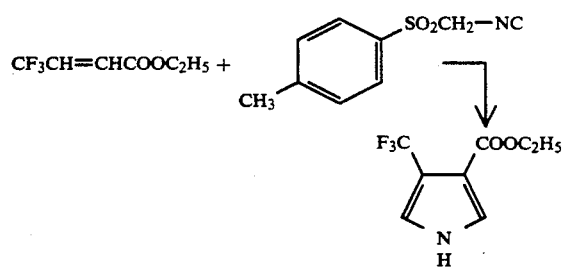

A solution of potassium t-butoxide (8.11 g, 0.075 mol) in tetrahydrofuran at −60° C. is treated dropwise with a mixture of ethyl 4,4,4-trifluorocrotonate (10.5 g, 0.063 mol) and p-tolylsulfonylmethylisocyanide (12.2 g, 0.063 mol) in tetrahydrofuran over a 1 hour period, stirred at −60° C. for 30 minutes, allowed to warm to room temperature and quenched with water. The reaction mixture is extracted with ether and ethyl acetate. The combined extracts are washed with brine, dried (MgSO4) and concentrated in vacuo to give a solid residue. Recrystallization from 1,2-dichloroethane affords the title compound as a tan solid, 7.3 g (56%), mp 163°-164° C.

EXAMPLE 32

Preparation of ethyl 1-methyl-4-(trifluoromethyl)pyrrole-3-carboxylate

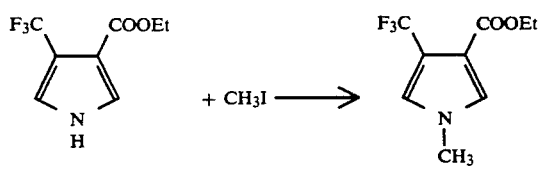

A solution of potassium t-butoxide (4.5 g, 0.04 mol) in tetrahydrofuran is treated dropwise with a solution of ethyl 4-(trifluoromethyl)pyrrole-3-carboxylate (8.3 g, 0.04 mol) in tetrahydrofuran over a 20 minute period at 20°-25° C., stirred for 30 minutes, treated dropwise with methyl iodide (5.7 g, 0.04 mol), stirred at room temperature for 24 hours and poured into water. The resultant mixture is extracted with ether and the combined extracts are washed with brine, dried (MgSO4) and concentrated in vacuo to afford a brown oil residue. The residue is distilled using a Kugelrohr distillation apparatus to give a gummy solid at 80°-85° C./0.2 mm Hg. The solid is purified using ether and basic alumina to yield the title compound as a clear oil, 6.37 g (72%), identified by NMR and elemental analyses.

EXAMPLE 33

Preparation of 1-methyl-4-(trifluoromethyl)pyrrole-3-carboxylic acid

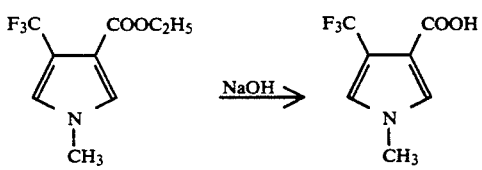

A mixture of ethyl 1-methyl-4-(trifluoromethyl)pyrrole-3-carboxylate (4.4 g, 0.02 mol) and 4N sodium hydroxide (5 ml, 0.02 mol) in ethanol is stirred for 24 hours at room temperature, diluted with water and extracted with ether. The aqueous phase is acidified with 10% HCl and filtered. The filter cake is washed with water and dried in vacuo at 45° C. to afford the title compound as an off-white solid, 2.4 g (62%), mp 210°-212° C.

EXAMPLE 34

Preparation of 1-methyl-4-(trifluoromethyl)pyrrole-3-carbonitrile

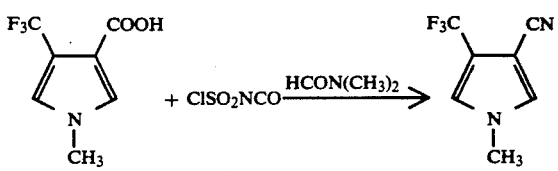

A mixture of 1-methyl-4-(trifluoromethyl)pyrrole-3-carboxylic acid (1.93 g, 0.01 mol) in acetonitrile at 40°-45° C. is treated dropwise with chlorosulfonylisocyanate (1.41 g, 0.01 mol), heated at 40° C. for 24 hours, cooled to room temperature, treated with dimethylformamide (1.46 g, 0.02 mol), heated at 40° C. for 8 hours, cooled to room temperature, stirred for 48 hours at room temperature and poured into water. The resultant mixture is extracted with ethyl acetate. The extracts are combined, washed sequentially with water and brine, dried (MgSO$_4$) and concentrated in vacuo to afford an oily solid residue. The residue is taken up in ethyl acetate, washed with 1% aqueous sodium hydroxide, dried (MgSO$_4$) and concentrated in vacuo to give a yellow oil residue. Kugelrohr distillation at 100°-110° C./2 mm Hg yields the title product as a white solid, 0.95 g (54%).

EXAMPLE 35

Preparation of phenyl 2,3,5-tribromo-4-cyanopyrrole-1-carboxylate

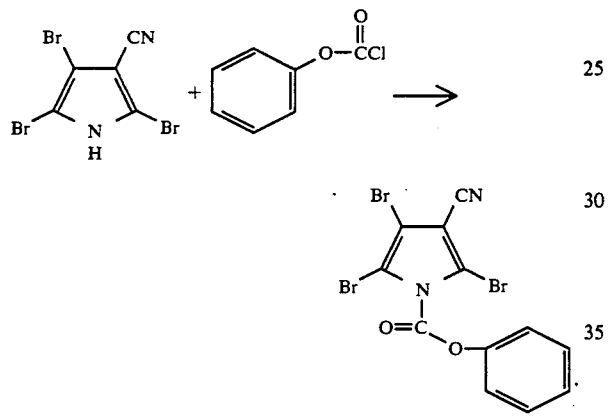

A mixture of 7.0 g of 2,4,5-tribromopyrrole-3-carbonitrile and 2.9 g of potassium t-butoxide in tetrahydrofuran is treated with 13.8 g of phenyl chloroformate, heated at reflux temperature for 12 hours, cooled, poured into water and filtered. The solid filter cake is washed with water and dried in vacuo to afford the title compound A sample is recrystallized from a mixture of ethyl acetate and methylcyclohexane to give colorless crystals, mp 128°-129° C.

EXAMPLE 36

Preparation of methyl 2,3,5-tribromo-4-cyanopyrrole-1-carboxylate

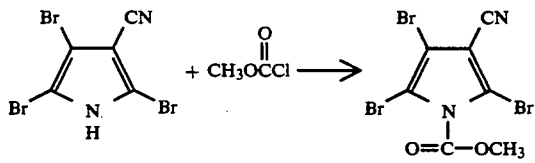

A solution of 2,4,5-tribromopyrrole-3-carbonitrile (3.0 g, 0.091 mol) in tetrahydrofuran is treated portionwise with potassium t-butoxide (1.33 g, 0.012 mol) at room temperature, stirred for 20 minutes, treated dropwise with a solution of methyl chloroformate (1.29 g, 0.014 mol) in tetrahydrofuran, stirred for 2½ days, poured into water and extracted with ether. The combined ether extracts are washed with brine, dried over MgSO$_4$ and concentrated in vacuo to give a brown solid residue. The residue is recrystallized from ethyl acetate/hexanes to afford the title compound as a tan solid, 1.4 g (39.5%) mp 119.5°-122.0° C.

Using the above procedure and substituting the appropriate chloroformate, the following compounds are obtained:

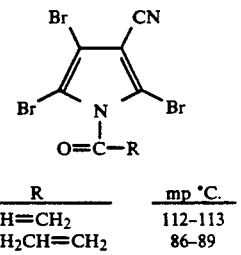

| R | mp °C. |
|---|---|
| OCH=CH$_2$ | 112-113 |
| OCH$_2$CH=CH$_2$ | 86-89 |

EXAMPLE 37

Preparation of 2,4,5-tribromo-1-(p-chlorobenzoyl)-pyrrole-3-carbonitrile

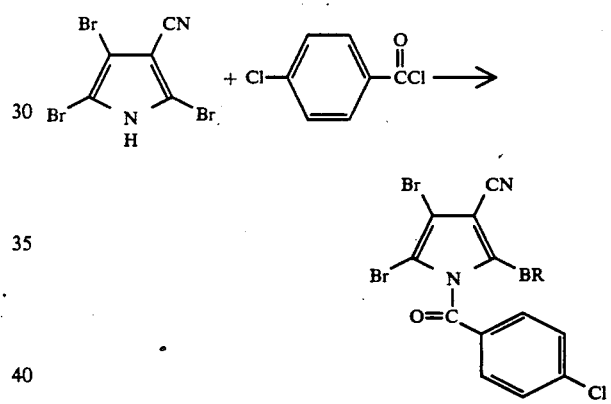

A mixture of 2,4,5-tribromopyrrole-3-carbonitrile (5.0 g, 0.015 mol) and potassium t-butoxide (2.0 g, 0.018 mol) in dry tetrahydrofuran is stirred for 10 minutes at room temperature, treated dropwise with a solution of p-chlorobenzoyl chloride (3.25 g, 0.018 mol) in tetrahydrofuran, heated at reflux temperature for 3 hours, cooled and diluted with a mixture of water and ethyl acetate. The organic phase is separated, washed with brine, dried over Na$_2$SO$_4$ and concentrated in vacuo to afford a tan solid residue. Recrystallization from benzene gives the title compound as a cream colored solid, 2.9 g (41.4%), mp 154°-157° C.

Using the above procedure and substituting p-methoxybenzoyl chloride gives 2,4,5-tribromo-1-(p-methoxybenzoyl)pyrrole-3-carbonitrile, mp 86°-89° C.

EXAMPLE 38

Insecticidal and acaricidal evaluations of cyano and nitropyrroles

In these tests evaluations are performed using technical material dissolved in 50/50 acetone water mixtures. All concentrations reported herein are in terms of active ingredient. All tests are conducted in a laboratory maintained at about 27° C. The rating system employed is as follows:

| Rating System | |
|---|---|
| 0 = no effect | 5 = 56-65% kill |
| 1 = 10-25% kill | 6 = 66-75% kill |
| 2 = 26-35% kill | 7 = 76-85% kill |
| 3 = 36-45% kill | 8 = 86-99% kill |
| 4 = 46-55% kill | 9 = 100% kill |
| | R = reduced feeding |

The test species of insects and acarids used in the present evaluations along with specific test procedures are described below.

*Spodoptera eridania*, 3rd instar larvae, southern armyworm

A Sieva lima bean leaf expanded to 7-8 cm in length is dipped in the test solution with agitation for 3 seconds and placed in a hood to dry. The leaf is then placed in a 100×10 mm petri dish containing a damp filter paper on the bottom and ten 3rd instar caterpillars. The dish is maintained for 5 days before observations are made of mortality, reduced feeding, or any interference with normal moulting.

*Spodoptera eridania*, 7-day residual

The plants treated in the above Test are maintained under high intensity lamps in the greenhouse for 7 days. These lamps duplicate the effects of a bright sunny day in June in New Jersey and are kept on for 14 hour day length. After 7 days, the foliage is sampled and assayed as in the above-said Test.

*Aphis fabae*, mixed instar, bean aphid

Pots containing single nasturtium plants (Tropaeolum sp.) about 5 cm tall are infested with about 100-200 aphids one day before the test. Each pot is sprayed with the test solution for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

*Tetranychus urticae* (P-resistant strain), 2-spotted spider mite

Sieva lima bean plants with primary leaves expanded to 7-8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test solution for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

*Diabrotic undecimpunctata howardi*, 3rd instar southern corn rootworm

One cc of fine talc is placed in a 30 ml wide-mouth screw-top glass jar. One ml of the appropriate acetone solution is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 ml of moist soil is added to each jar. The jar is capped and the contents thoroughly mixed on a Vortex Mixer. Following this, ten 3rd instar root-worms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

Data obtained are reported in Table I below.

Where two or more tests are conducted with a given compound the ratings are averaged. Also, where no tests have been conducted, the evaluation is shown as a dash (—).

TABLE I

| | Insecticidal and Acaricidal Evaluations | | | | | | |
|---|---|---|---|---|---|---|---|
| | Bean Aphids | Armyworms | | | P. Resistant Mites PPM | | SCRW[1] kg/ha |
| | | Initial PPM | | 1000 PPM @ 7 | | | |
| Compound | 100 PPM | 1000 | 100 | Days | 300 | 100 | 50 |
| 2,4,5-trichloro-pyrrole-3-carbonitrile | 0 | 9 | 9 | 9 | 9 | 9 | 0 |
| 2,4,5-tribromo-pyrrole-3-carbonitrile | 9 | 9 | 6.5 | — | 8 | — | 0 |
| 2,4,5-trichloro-1-methylpyrrole-3-carbonitrile | 0 | 9 | 4.5 | 6.5 | 9 | 9 | 0 |
| 2,4,5-tribromo-1-methylpyrrole-3-carbonitrile | 9 | 9 | 9 | 0 | 9 | 9 | 5 |
| 2,4,5-tribromo-pyrrole-1,3-dicarbonitrile | 8.5 | 9 | 9 | — | 9 | 9 | — |
| 2,4,5-triiodo-1-methylpyrrole-3-carbonitrile | 0 | 9 | — | — | 0 | — | — |
| 3,4,5-tribromo-pyrrole-2-carbonitrile | 9 | 9 | 0 | 9 | 9 | — | — |
| 3,4,5-tribromo-1-methylpyrrole-2- | 6 | 9 | 0 | — | 9 | 9 | 9 |

TABLE I-continued

| | Insecticidal and Acaricidal Evaluations | | | | | | |
|---|---|---|---|---|---|---|---|
| | Bean Aphids | Armyworms | | | P. Resistant Mites PPM | | SCRW[1] kg/ha |
| | | Initial PPM | | 1000 PPM @ 7 | | | |
| Compound | 100 PPM | 1000 | 100 | Days | 300 | 100 | 50 |
| carbonitrile | | | | | | | |
| 3,4-dibromo-5-nitropyrrole-2-carbonitrile | 0 | 9 | 0 | — | 0 | — | 0 |
| 3,5-dibromo-4-nitropyrrole-2-carbonitrile | 0 | 7 | 0 | — | 0 | — | 0 |
| 1-benzyl-2,4,5-trichloropyrrole-3-carbonitrile | 0 | 3.5 | 0 | — | 8.5 | 9 | — |
| 2,4,5-tribromo-1-(2-propynyl)pyrrole-3-carbonitrile | 0 | 9 | 1 | — | 9 | 9 | — |
| 2,4,5-tribromo-1-(ethoxymethyl)pyrrole-3-carbonitrile | 0 | 9 | 9 | 9 | 9 | 9 | — |
| 3,5-dibromopyrrole-2,4-dicarbonitrile | 0 | 9 | 6 | 0 | 0 | — | 0 |
| 2,4,5-triiodopyrrole-3-carbonitrile | 5 | 9 | 9 | 7.5 | 8 | 7 | 0 |
| 5-nitropyrrole-2-carbonitrile | 9 | 9 | 0 | 6 | 9 | 9 | 9 |
| 4-nitropyrrole-2-carbonitrile | 0 | 9 | 0 | 9 | 9 | 8 | 0 |
| 2,4,5-tribromo-1-ethylpyrrole-3-carbonitrile | 0 | 9 | — | — | 9 | — | 4 |
| 1-allyl-2,4,5-tribromopyrrole-3-carbonitrile | 9 | 0 | — | — | 9 | — | 0 |
| 1-methyl-5-nitropyrrole-2-carbonitrile | 0 | 4 | — | — | — | — | 0 |
| 1-(ethoxymethyl)-5-nitropyrrole-2-carbonitrile | 0 | 0 | — | — | — | — | 9 |
| pyrrole-2,4-dicarbonitrile | 0 | 9 | 9 | 4 | 0 | — | 0 |
| 2-chloro-4-nitropyrrole | 0 | 4 | — | — | 9 | 0 | 0 |
| 2,5-dichloro-3-nitropyrrole | 0 | 9 | 0 | — | 9 | 0 | 6 |
| 2,3-dichloro-4-nitropyrrole | 0 | 9 | 0 | — | 9 | 0 | 0 |
| 2,3,5-trichloro-4-nitropyrrole | 0 | 9 | 0 | — | 9 | 5 | 0 |
| 3,4,5-tribromo-1-(2-propynyl)pyrrole-2-carbonitrile | 9 | 9 | 9 | 0 | 9 | 0 | 9 |
| 4,5-dibromo-1-methyl-2-(trifluoromethyl)pyrrole-3-carbonitrile | — | 0 | — | — | 8 | — | — |
| 4,5-dibromo-2-(trifluoromethyl)pyrrole-3-carbonitrile | 7.5 | 9 | 0 | 9 | 9 | 9 | 9 |
| 4,5-dibromo-1-methylpyrrole-3-carbonitrile | 0 | 5.5 | 0 | — | 8.5 | 6 | 0 |
| 2,4,5-tribromo-1-cyanoethylpyrrole-3-carbonitrile | 0 | 9 | — | — | 0 | — | 0 |
| 3,4,5-tribromo-1-(2-propynyl)pyrrole-2-carbonitrile | 9 | 9 | 9 | — | 9 | 0 | 9 |
| 1-methyl-4-(trifluoromethyl)pyrrole-3-carbonitrile | 0 | 0 | — | — | 0 | — | 0 |
| 4,5-dibromo-1-methylpyrrole-3-carbonitrile | 0 | 6 | 0 | — | 9 | 6 | 0 |
| 2,3,5-tribromo-4-cyanopyrrole-1-acetonitrile | 0 | 9 | 0 | — | 0 | — | 0 |

TABLE I-continued

| | Insecticidal and Acaricidal Evaluations | | | | | | |
|---|---|---|---|---|---|---|---|
| | Bean Aphids | Armyworms | | | P. Resistant Mites PPM | | SCRW[1] kg/ha |
| | | Initial PPM | | 1000 PPM @ 7 | | | |
| Compound | 100 PPM | 1000 | 100 | Days | 300 | 100 | 50 |
| 1-(ethoxymethyl)-2-(trifluoromethyl)-pyrrole-3-carbonitrile | 0 | 0 | — | — | 0 | — | 6 |
| 2,4,5-tribromo-1-(1-methoxyethyl)pyrrole-3-carbonitrile | 0 | 9 | 9 | 0 | 9 | 8 | 0 |
| 4,5-dibromo-1-(ethoxymethyl)-2-(trifluoromethyl)pyrrole-3-carbonitrile | 9 | 9 | 9 | — | 9 | 9 | 9 |
| 4-(trifluoromethyl)-pyrrole-3-carbonitrile | 0 | 0 | — | — | 0 | — | 0 |
| 2,5-dibromo-4-(trifluoromethyl)pyrrole-3-carbonitrile | 0 | 9 | 0 | — | 9 | 9 | 0 |
| 2,5-dibromo-1-methyl-4-(trifluoromethyl)-pyrrole-3-carbonitrile | 0 | 9 | 0 | — | 5 | 0 | 9 |
| 4-bromo-1-t-butyl-pyrrole-3-carbonitrile | 0 | 0 | — | — | 0 | — | 0 |
| 2,4,5-tribromo-1-(hydroxymethyl)pyrrole-3-carbonitrile, pivalate (ester) | 0 | 9 | — | — | 9 | — | — |
| 4,5-dibromo-1-methyl-pyrrole-2-carbonitrile | 0 | 9 | 0 | — | 9 | 0 | — |
| 4,5-dibromopyrrole-2-carbonitrile | 0 | 9 | 9 | — | 9 | — | — |
| 4,5-diiodo-1-methylpyrrole-2-carbonitrile | 0 | 9 | 0 | — | 0 | — | — |

[1]SCRW designates southern corn rootworm

EXAMPLE 39

Insecticidal Evaluations

Insecticidal evaluations are conducted with solutions of test compounds dissolved or dispersed in 50/50 acetone/water mixtures. The test compound is technical material dissolved or dispersed in said acetone/water mixtures in sufficient amount to provide the concentrations set forth in Table II below. The rating system used is the same rating system described in Example 25 The procedures employed are described below for evaluation against specific insect species Where two or more tests are conducted using the same compound, the average of test results is reported.

*Empoasca abrupta*, adults, western potato leafhopper

A Sieva lima bean leaf about 5 cm long is dipped in the test solution for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

*Heliothis virescens*, 3rd instar tobacco budworm

Cotton cotyledons are dipped in the test solution and allowed to dry in a hood. When dry, each is cut into quarters and ten sections placed individually in 30 ml plastic medicine cups containing a 5-7 mm long piece of damp dental wick. One third-instar caterpillar is added to each cup and a cardboard lid placed on the cup. Treatments are maintained for 3 days before mortality counts and estimates of reduction in feeding damage are made.

*Spodoptera eridania*, systemic uptake, 3rd instar larvae, southern armyworm

The compound is formulated as an emulsion containing 0.1 gm of the test material, 0.2 gm of Emulphor EL-620® emulsifier, 10 ml of acetone and 90 ml of water. This is diluted 10-fold with water to give a 100 ppm emulsion for the test. Subsequent 10-fold dilutions are made with water as needed. Sieva lima bean plants, with the primary leaves expanded to a length of 7-8 cm, are cut off at least 3 cm above the soil level to avoid contamination with soil bacteria that will cause decay of the stem during the test. The cut stems are placed in the test emulsions and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish with 10 southern armyworms. Mortality counts and observations of feeding damage are made 3 and 5 days later. The same procedure is following for evaluation of test compounds against *Empoasca abruota*, Adults, Western Potato Leafhoppers. Data obtained are reported in Table II below.

*Blattella germanica*, bait test, adult male German cockroach

A 0.1% bait is prepared by pipetting 1 ml of a 1000 ppm solution of the test compound in acetone onto 1 gram of cornmeal in a 30 ml wide-mouth bottle. The bait is dried by passing a gentle stream of air into the bottle. The bait is placed in a 1 pint wide-mouth Mason jar and ten adult male cockroaches are added. A screen lid is placed on the jar and a small piece of cotton soaked in 10% honey is put on the top of the screen lid. Mortality counts are made after 3 days.

*Blattella germanica*, residue test, adult male German cockroach

One ml of a 1000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

Data obtained are reported in Table II and Table III below.

TABLE II

| | Insecticidal Evaluations | | | | | | |
|---|---|---|---|---|---|---|---|
| | | TBW[1] | | C-S[2] SYSTEMIC | | G. COCKROACH | |
| | LEAF HOPPER | ppm | | SAW[3] | LEAF HOPPER | BAIT | RES. |
| Compound | ppm 100 | 1000 | 100 | ppm 100 | ppm 100 | ppm 1000 | ppm 1000 |
| 2,4,5-trichloro-pyrrole-3-carbonitrile | 9 | 8 | 0 | 4 | — | 0 | 9 |
| 2,4,5-tribromo-pyrrole-3-carbonitrile | 0 | 9 | 0 | 0 | 9 | 0 | 9 |
| 2,4,5-trichloro-1-methylpyrrole-3-carbonitrile | 5 | — | 0 | 0 | 8.5 | 9 | 4.5 |
| 2,4,5-tribromo-1-methylpyrrole-3-carbonitrile | 9 | 9 | 0 | 5 | 0 | 0 | 9 |
| 2,4,5-tribromo-pyrrole-1,3-dicarbonitrile | 0 | 9 | 0 | 0 | 0 | 9 | 9 |
| 2,4,5-triiodo-1-methylpyrrole-3-carbonitrile | — | — | — | — | — | — | — |
| 3,4,5-tribromo-pyrrole-2-carbonitrile | 4 | 0 | — | 0 | 0 | 0 | 9 |
| 3,4,5-tribromo-1-methylpyrrole-2-carbonitrile | 0 | 9 | 0 | 5 | 9 | 9 | 9 |
| 3,4-dibromo-5-nitropyrrole-2-carbonitrile | 0 | 7 | — | — | — | 0 | 0 |
| 3,5-dibromo-4-nitropyrrole-2-carbonitrile | 0 | 4.5 | — | — | — | 0 | 0 |
| 1-benzyl-2,4,5-trichloropyrrole-3-carbonitrile | 0 | 0 | — | 0 | 9 | 0 | 7.5 |
| 2,4,5-tribromo-1-(2-propynyl)pyrrole-3-carbonitrile | 9 | 9 | — | 0 | 0 | 9 | 9 |
| 2,4,5-tribromo-1-(ethoxymethyl)pyrrole-3-carbonitrile | 4 | 9 | 0 | 0 | 0 | 9 | 9 |
| 3,5-dibromopyrrole-2,4-dicarbonitrile | 0 | 0 | — | 9 | 7 | 0 | 0 |
| 2,4,5-triiodopyrrole-3-carbonitrile | 0 | 9 | 9 | 0 | 0 | 6 | 9 |
| 5-nitropyrrole-2-carbonitrile | — | 9 | 5 | 0 | 9 | 0 | 9 |
| 4-nitropyrrole-2-carbonitrile | 8 | 6 | 0 | 9 | 9 | 0 | 9 |
| 2,4,5-tribromo-1-ethylpyrrole-3-carbonitrile | — | — | — | — | — | — | — |
| 1-allyl-2,4,5-tribromopyrrole-3-carbonitrile | — | — | — | — | — | — | — |
| 1-methyl-5-nitro-pyrrole-2-carbonitrile | — | 0 | — | 0 | — | 0 | 9 |
| 1-(ethoxymethyl)-5-nitropyrrole-2-carbonitrile | — | 0 | — | — | — | — | 9 |
| pyrrole-2-dicarbonitrile | 0 | 0 | 0 | 9 | 9 | 0 | 9 |
| 2-chloro-4-nitropyrrole | 0 | 0 | — | 0 | — | 0 | 9 |
| 2,5-dichloro-3-nitropyrrole | 0 | 0 | — | 0 | — | 0 | 7 |

TABLE II-continued

| | Insecticidal Evaluations | | | | | | |
|---|---|---|---|---|---|---|---|
| | LEAF HOPPER | TBW[1] ppm | | C-S[2] SYSTEMIC | | G. COCKROACH | |
| | | | | SAW[3] | LEAF HOPPER | BAIT | RES. |
| Compound | ppm 100 | 1000 | 100 | ppm 100 | ppm 100 | ppm 1000 | ppm 1000 |
| 2,3-dichloro-4-nitropyrrole | 0 | 7 | 2 | 0 | — | 0 | 9 |
| 2,3,5-trichloro-4-nitropyrrole | 0 | 0 | — | 0 | — | 0 | 9 |
| 3,4,5-tribromo-1-(2-propynyl)pyrrole-2-carbonitrile | 9 | 8 | 0 | 0 | — | 9 | 9 |
| 3,4,5-tribromo-1-(2-propynyl)pyrrole-2-carbonitrile | 9 | 9 | 9 | — | 9 | 0 | 9 |
| 1-methyl-4-(trifluoromethyl)pyrrole-3-carbonitrile | 0 | 0 | — | — | 0 | — | 0 |
| 4,5-dibromo-1-methylpyrrole-3-carbonitrile | 0 | 6 | 0 | — | 9 | 6 | 0 |
| 2,3,5-tribromo-4-cyanopyrrole-1-acetonitrile | 0 | 9 | 0 | — | 0 | — | 0 |
| 1-(ethoxymethyl)-2-(trifluoromethyl)-pyrrole-3-carbonitrile | 0 | 0 | — | — | 0 | — | 6 |
| 2,4,5-tribromo-1-(1-methoxyethyl)pyrrole-3-carbonitrile | 0 | 9 | 9 | 0 | 9 | 8 | 0 |
| 4,5-dibromo-1-(ethoxymethyl)-2-(trifluoromethyl)pyrrole-3-carbonitrile | 9 | 9 | 9 | — | 9 | 9 | 9 |
| 4-(trifluoromethyl)-pyrrole-3-carbonitrile | 0 | 0 | — | — | 0 | — | 0 |
| 2,5-dibromo-4-(trifluoromethyl)pyrrole-3-carbonitrile | 0 | 9 | 0 | — | 9 | 9 | 0 |
| 2,5-dibromo-1-methyl-4-(trifluoromethyl)-pyrrole-3-carbonitrile | 0 | 9 | 0 | — | 5 | 0 | 9 |
| 4-bromo-1-t-butyl-pyrrole-3-carbontrile | 0 | 0 | — | — | 0 | — | 0 |
| 2,4,5-tribromo-1-(hydroxymethyl)pyrrole-3-carbonitrite, pivalate (ester) | 0 | 9 | — | — | 9 | — | — |
| 4,5-dibromo-1-methyl-pyrrole-2-carbonitrile | 0 | 9 | 0 | — | 9 | 0 | — |
| 4,5-dibromopyrrole-2-carbonitrite | 0 | 9 | 9 | — | 9 | — | — |
| 4,5-diiodo-1-methylpyrrole-2-carbonitrile | 0 | 9 | 0 | — | 0 | — | — |

[1]TBW designates tobacco budworm
[2]C-S designates cut stem
[3]SAW designates southern armyworm

TABLE III

| | Insecticidal Evaluations | | | | G. COCKROACH | | |
|---|---|---|---|---|---|---|---|
| | LEAF HOPPER | TBW[1] | | | BAIT | | RES. |
| Compound | ppm 100 | ppm 1000 | ppm 100 | ppm 1000 | ppm 100 | ppm 1000 | ppm 100 |
| 3,4,5-tribromo-1-(2-propynyl)pyrrole-2-carbonitrile | 9 | 8 | 0 | 9 | 0 | 9 | 9 |
| 2,3,5-tribromo-4-cyano-pyrrole-1-acetonitrile | — | 9 | 0 | 9 | — | 9 | 9 |
| 1-(ethoxymethyl)-2-(trifluoromethyl)-pyrrole-3-carbonitrile | — | 3 | 0 | 0 | — | 0 | — |
| 2,4,5-tribromo-1-(1-methoxyethyl)-pyrrole-3-carbonitrile | 9 | 9 | 0 | 9 | — | 9 | 7 |
| 4,5-dibromo-1(ethoxymethyl)-2-(trifluoromethyl)pyrrole-3- | 9 | 0 | — | 0 | — | 9 | 2 |

TABLE III-continued

| | Insecticidal Evaluations | | | | | | |
|---|---|---|---|---|---|---|---|
| | LEAF HOPPER | TBW[1] | | G. COCKROACH | | | |
| | | | | BAIT | | RES. | |
| Compound | ppm 100 | ppm 1000 | ppm 100 | ppm 1000 | ppm 100 | ppm 1000 | ppm 100 |
| carbonitrile | | | | | | | |
| 2,5-dibromo-4-(tri-fluoromethyl)pyrrole-3-carbonitrile | 0 | 0 | — | 0 | — | 4 | 0 |
| 2,5-dibromo-1-methyl-4-(trifluoromethyl)-pyrrole-3-carbonitrile | 9 | — | 0 | — | 9 | — | 5 |
| 4,5-dibromo-1-methyl-pyrrole-2-carbonitrile | 4 | 0 | — | 3 | — | 0 | — |
| 4,5-dibromopyrrole-2-carbontrile | 0 | 0 | 0 | 0 | — | 9 | 8 |
| 4,5-diiodo-1-methyl-pyrrole-2-carbonitrile | 9 | 0 | 0 | 0 | — | 0 | — |

[1]TBW designates tobacco budworm

EXAMPLE 40

Evaluation of test compounds for the control of slugs. species Arion subfuscus

Evaluation A

A 5% bait of each test compound is prepared by mixing 0.10 gms of technical material with 1.90 gms of a bait consisting of 46% unprocessed bran, 6% molasses, and 48% water. One test arena is set up for each treatment by placing 2.0 gms of the bait into a lid from a one-ounce jar, and placing the lid into a moist filter-paper lined, eight-ounce, wax-paper cup. Each cup is infested with 5, field-collected slugs, *Arion subfuscus*. A plastic lid, with pin holes through it, is placed over the top of each cup. The test is set up and infested with the field-collected slugs. Test treatments are examined periodically and mortality readings taken after 3 and 4 days. Slugs that do not respond to prodding are considered dead. Slugs which respond much more slowly than the untreated control slugs are considered moribund.

| Compound | Percent Mortality of Arion subfuscus |
|---|---|
| 2,4,5-Tribromopyrrole-3-carbonitrile | 100 |
| 2,4,5-Trichloro-1-methyl-pyrrole-3-carbonitrile | 100 |
| 2,4,5-Tribromo-1-methyl pyrrole-3-carbonitrile | 100 |
| 1-Benzyl-2,4,5-Trichloro-pyrrole-3-carbonitrile | 100 |
| 1-Benzyl-2,4,5-Tribromo-pyrrole-3-carbonitrile | 100 |
| 2,4,5-Tribromopyrrole-1,3-dicarbonitrile | 100 |
| 1-(Ethoxymethyl)-5-nitro-pyrrole-2-carbonitrile | 100 |

Evaluation B

Test compounds are weighed and diluted in acetone to achieve the desired concentration, and 1.0 ml of each test solution is added to 1.0 g of unprocessed bran. The acetone is then removed by evaporation. The bait composition is prepared by mixing 1.0 g of the above-said treated unprocessed bran with 1.0 ml of a molasses mixture consisting of 4.0 ml molasses and 30.0 ml water. The thus-prepared bait composition is placed into the lid of a 1 oz jar which is then placed onto the bottom of an 8 oz waxed paper cup which has been lined with wet filter paper. Each cup is then infested with 5 slugs. A control cup which contains 0% test compound in the bait composition is also prepared and infested. Test treatments are examined daily for 4 days and feeding and mortality rates are recorded. The data obtained are shown below.

| | % Mortality of Arion subfuscus (% Bait) | | | | |
|---|---|---|---|---|---|
| Compound | 5.0% | 1.0% | 0.3% | 0.1% | 0.03% |
| 2,4,5-Tribromo-1-methyl-pyrrole-3-carbonitrile | 100 | 100 | 100 | 100 | 35 |
| 2,4,5-Tribromo-1-(hydroxymethyl)-pyrrole-3-carbonitrile, pivalate (ester) | 100 | 100 | 100 | 100 | 80 |
| 1-Benzyl-2,4,5-tribromopyrrole-3-carbonitrile | — | 100 | 100 | 60 | 0 |
| 3,4,5-Tribromo-1-(2-propynyl)pyrrole-2-carbonitrile | — | 100 | 100 | 0 | — |
| 2,4,5-Triiodopyrrole-3-carbonitrile | — | 100 | $20^R$ | 0 | — |
| Pyrrole-3,4-dicarbonitrile | — | 100 | 0 | 0 | — |
| 3,4,5-Tribromo-1-methylpyrrole-2-carbonitrile | 100 | — | — | 100 | 0 |
| 2,4,5-Tribromo-pyrrole-3-carbonitrile | 100 | 0 | — | — | — |
| 2,4,5-Trichloro-1-methyl-pyrrole-3-carbonitrile | 100 | — | — | — | — |
| 2,4,5-Tribromo-pyrrole-1,3-dicarbonitrile | 100 | — | — | 70 | 60 |
| 1-(Ethoxymethyl)-5-nitropyrrole-2-carbonitrile | 100 | — | — | — | — |
| 3,4,5-Tribromo-pyrrole-2-carbonitrile | 100 | $0^R$ | — | — | — |
| 2,3,5-Tribromo-4-cyanopyrrole-1-acetonitrile | — | 100 | 0 | — | — |
| 2,4,5-Tribromo-1-ethylpyrrole-3-carbonitrile | — | 100 | 100 | 70 | 0 |
| 1-Allyl-2,4,5-tribromopyrrole-3-carbonitrile | — | 100 | 100 | 87 | 10 |
| 2,4,5-Tribromo-1-(p-chlorobenzyl)-pyrrole-3-carbo- | — | 100 | 100 | 100 | — |

-continued

| Compound | % Mortality of Arion subfuscus (% Bait) | | | | |
|---|---|---|---|---|---|
| | 5.0% | 1.0% | 0.3% | 0.1% | 0.03% |
| nitrile | | | | | |
| 2,4,5-Tribromo-1-(2-chloro-1-ethoxyethyl)pyrrole-3-carbonitrile | — | 100 | 100 | 100 | 100 |
| 2,4,5-Tribromo-1-(hydroxymethyl)pyrrole-3-carbonitrile, acetate | — | 100 | 100 | 100 | 100 |
| 2,4,5-Tribromo-1-[(trimethylsilyl)methyl]pyrrole-3-carbonitrile | — | 100 | 100 | 100 | — |
| 2,4,5-Tribromo-1-(p-chlorobenzoyl)pyrrole-3-carbonitrile | — | 100 | 100 | 100 | 0 |
| Phenyl 2,3,5-tribromo-4-cyanopyrrole-1-carboxylate | — | 100 | 100 | 100 | 40 |
| 3,4,5-Tribromo-1-methylpyrrole-2-carbonitrile | — | 100 | 100 | 100 | 0 |
| 2,4,5-Tribromo-1-(isopropoxymethyl)pyrrole-3-carbonitrile | — | 100 | 100 | 100 | 60 |
| 2,4,5-Tribromo-1-(ethoxymethyl)pyrrole-3-carbonitrile | — | 100 | 100 | 100 | 100 |

R designates reduced feeding

EXAMPLE 41

Evaluation of pyrrole carbonitriles and nitropyrroles as control agents for terrestrial snails-species: Helix aspersa

*Helix aspersa*, commonly known as brown garden snails, are purchased from Ward's Biological Supply Company. Test compounds are then prepared as bait formulations as follows: The 5% bait is prepared by mixing technical material (50 mg) in a bran bait (950 mg) The bait is made with 46% unprocessed bran, 6% molasses and 48% water. The treated bait is placed in a 7 ml polystyrene weighing boat. The bait station is put in a 500 ml plastic deli container with one moistened dental wick. Two snails are then added to each treatment and a clear plastic lid with aeration holes is firmly placed on top of each container. The containers are examined 24 hours after the test is initiated and data obtained reported in the table below as % mortality.

| Compound | Percent Mortality of Helix aspersa 24 hours |
|---|---|
| 2,3-Dichloro-4-nitropyrrole | 100 |
| 2,3,5-Trichloro-4-nitropyrrole | 100 |
| 2,4,5-Tribromopyrrole-3-carbonitrile | 100 |
| 2,4,5-Trichloro-1-methylpyrrole-3-carbonitrile | 100 |
| 2,4,5-Tribromo-1-methylpyrrole-3-carbonitrile | 100 |
| 2,4,5-Tribromo-1-(2-propynyl)pyrrole-3-carbonitrile | 100 |
| 2,4,5-Tribromo-1-(ethoxymethyl)pyrrole-3-carbonitrile | 50 |
| 3,4,5-Tribromopyrrole-3-carbonitrile | 100 |
| 3,4,5-Tribromo-1-methylpyrrole-2-carbonitrile | 100 |

-continued

| Compound | Percent Mortality of Helix aspersa 24 hours |
|---|---|
| 2-carbonitrile | |

EXAMPLE 42

Land Snail Experiment with pyrrole carbonitriles

*Bulimulus maria* (Land Snails from Carolina Biological Supply Company, Code L480) are tested in 30 ml wide mouth jars. A 5% bait with cornmeal is used i.e. 25 mg of compound mixed in 450 mg cornmeal. The bait is moistened every two days. One snail is added to each jar and the caps are loosely placed on top. Fecal matter indicate feeding. Mortality is observed by probing the animal with a spatula. If the animal is alive contractions are evident Oozing and/or complete withdraw into the shell indicates mortality.

| Observations: | |
|---|---|
| Compound | % Mortality 1 Week |
| 2,4,5-Tribromo-1-methylpyrrole-3-carbonitrile | 100 |

EXAMPLE 43

Pyrrole Activity on Fresh Water Snails

Gyraulis fresh water aquatic snails are used to test the activity of the pyrroles. The snails are collected and maintained in a tank filled with pond water which is aerated with a bottom filter. Members of the pyrrole series are made up in aerated tap water (pH similar to pond water) at two dosages, 100 and 33 ppm. The compounds have relatively low solubility in water at 100 ppm but with stirring and sonication, solubility is greatly improved. Three healthy snails are added to each 150 ml beaker containing 80 milliliters of treated water. The concentrations tested are 100 and 33 ppm. An untreated check is also included.

| Observations: | | |
|---|---|---|
| Compound | PPM | % Mortality 18 Hours |
| 2,4,5-Tribromopyrrole-3-carbonitrile | 100 | 100 |
| | 33 | 100 |
| 2,4,5-Trichloro-1-methylpyrrole-3-carbonitrile | 100 | 100 |
| | 33 | 100 |
| 2,4,5-Tribromo-1-methylpyrrole-3-carbonitrile | 100 | 100 |
| | 33 | 100 |

EXAMPLE 44

Pyrrole Activity on Pond Snails

Physa pond snails, obtained from Ward's Biological Supply Company, are used to assay the arylpyrroles. Members of the pyrrole carbonitrile series are made up on aerated tap water at two dosages, 10 and 1 ppm. Three healthy snails are immersed in 10 milliliters of treated water in 20 milliliter scintillation vials. Caps are loosely placed on each vial.

| Compound | PPM | % Mortality 18 Hours |
|---|---|---|
| 2,4,5-Tribromopyrrole-3-carbonitrile | 10 | 100 |
| | 1 | 100 |
| 2,4,5-Tribromo-1-methyl-pyrrole-3-carbonitrile | 10 | 100 |
| | 1 | 100 |

What is claimed is:

1. A method for the control of insect, acarid or mollusk pests which comprises contacting said pests, or their food supply, breeding grounds or habitat infested with said pests, with a pesticidally effective amount of a pyrrole carbonitrile or nitropyrrole compound, wherein said compound has the structure:

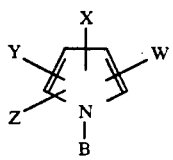

wherein
W is CN or $NO_2$;
X is CN, Br, Cl, I or $CF_3$;
Y is H, Br, Cl, I or $CF_3$;
Z is H, Br, Cl or I; and
B is

hydrogen,
$C_1$–$C_6$ alkyl unsubstituted or substituted with one to three halogen atoms,
one tri($C_1$–$C_4$alkyl)silyl,
one hydroxy,
one cyano,
one or two $C_1$–$C_4$ alkoxy groups unsubstituted or substituted with one to three halogen atoms,
one $C_1$–$C_4$ alkylthio,
one phenyl unsubstituted or substituted with one to three halogen atoms, one to three $C_1$–$C_4$ alkyl groups or one to three $C_1$–$C_4$ alkoxy groups,
one phenoxy group unsubstituted or substituted with one to three halogen atoms, one to three $C_1$–$C_4$ alkyl groups or one to three $C_1$–$C_4$ alkoxy groups,
one benzyloxy group unsubstituted or substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group unsubstituted or substituted with one to three halogen atoms,
one $C_{2l}$–$C_6$ alkenylcarbonyloxy group unsubstituted or substituted with one to three halogen atoms,
one phenylcarbonhyloxy group unsubstituted or substituted with one to three halogen atoms, one to three $C_1$–$C_4$ alkyl groups or one to three $C_1$–$C_4$ alkoxy groups,
one $C_1$–$C_6$ alkoxycarbonyl group unsubstituted or substituted with one to three halogen atoms or one to three $C_1$–$C_4$ alkoxy groups, or
one benzyloxycarbonyl group unsubstituted or substituted on the phenyl ring with one to three halogen atoms, one to three $C_1$–$C_4$ alkyl groups or one to three $C_1$–$C_4$ alkoxy groups,
$C_3$–$C_6$ alkenyl unsubstituted or substituted with one to three halogen atoms or one phenyl group,
$C_3$–$C_6$ alkynyl unsubstituted or substituted with one to three halogen atoms or one phenyl group or cyano;

R is $C_1$–$C_6$ alkyl unsubstituted or substituted with one to three halogen atoms,
one hydroxy,
one cyano,
one or two $C_1$–$C_4$ alkoxy groups unsubstituted or substituted with one to three halogen atoms,
one $C_1$–$C_4$ alkylthio,
one phenyl unsubstituted or substituted with one to three halogen atoms, one to three $C_1$–$C_4$ alkyl groups or one to three $C_1$–$C_4$ alkoxy groups,
one phenoxy group unsubstituted or substituted with one to three halogen atoms, one to three $C_1$–$C_4$ alkyl groups or one to three $C_1$–$C_4$ alkoxy groups,
one benzyloxy group unsubstituted or substituted on the phenyl ring with one to three halogen atoms, one to three $C_1$–$C_4$ alkyl groups or one to three $C_1$–$C_4$ alkoxy groups,
one $C_1$–$c_6$ alkylcarbonyloxy group unsubstituted or substituted with one to three halogen atoms,
one $C_2$–$C_6$ alkenylcarbonyloxy group unsubstituted or substituted with one to three halogen atoms,
one phenylcarbonyloxy group unsubstituted or substituted with one to three halogen atoms, one to three $C_1$–$C_4$ alkyl groups or one to three $C_1$–$C_4$ alkoxy groups,
one $C_1$–$C_6$ alkoxycarbonyl group unsubstituted or substituted with one to three halogen atoms or one to three $C_1$–$C_4$ alkoxy groups, or
one benzyloxycarbonyl group unsubstituted or substituted on the phenyl ring with one to three halogen atoms, one to three $C_1$–$C_4$ alkyl groups or one to three $C_1$–$C_4$ alkoxy groups,
$C_3$–$C_6$ alkenyl unsubstituted or substituted with one to three halogen atoms or one phenyl group,
$C_3$–$C_6$ alkynyl unsubstituted or substituted with one to three halogen atoms or one phenyl group,
phenyl unsubstituted or substituted with one to three halogen atoms, one or two $C_1$–$C_4$ alkyl groups, one or two $C_1$–$C_4$ alkoxy groups, $CF_3$, CN, $NO_2$, di($C_1$–$C_4$ alkyl)amino or $C_1$–$C_4$ alkanoylamino,
phenoxy unsubstituted or substituted with one to three halogen atoms, one or two $C_1$–$C_4$ alkyl groups, one or two $C_1$–$C_4$ alkoxy groups, $CF_3$, CN, $NO_2$, di($C_1$–$C_4$ alkyl)amino or $C_1$–$C_4$ alkanoylamino,
$C_1$–$C_6$ alkoxy unsubstituted or substituted with one to three halogen atoms,
$C_2$–$C_6$ alkenyloxy unsubstituted or substituted with one to three halogen atoms,
di($C_1$–$c_4$ alkyl)amino,
N-($C_1$–$C_4$ alkyl)-N-phenylamino or N-($C_1$–$C_4$ alkyl)-N-halophenylamino, or
$C_3$–$C_6$ polymethyleneimino;
provided that when W is CN in the 2-position and B is hydrogen, then Y and Z cannot be hydrogen in the compound for the control of mollusk pests.

2. The method according to claim 1, wherein B is hydrogen.

3. The method according to claim 1, wherein B is $C_1$–$C_6$ alkyl unsubstituted or substituted with one to three halogen atoms,
one tri($C_1$–$C_4$ alkyl)silyl,
one hydroxy,
one cyano,
one to two $C_1$–$C_4$ alkoxy groups unsubstituted or substituted with one to three halogen atoms,
one $C_1$–$C_4$ alkylthio,
one phenyl unsubstituted or substituted with one to three halogen atoms, one to three $C_1$–$C_4$ alkyl groups or one to three $C_1$–$C_4$ alkoxy groups,
one phenoxy group unsubstituted or substituted with one to three halogen atoms, one to three $C_1$–$C_4$ alkyl groups or one to three $C_1$–$C_4$ alkoxy groups,
one benzyloxy group unsubstituted or substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group unsubstituted or substituted with one to three halogen atoms,
one $C_2$–$C_6$ alkenylcarbonyloxy group unsubstituted or substituted with one to three halogen atoms,
one phenylcarbonyhloxy group unsubstituted or substituted with one to three halogen atoms, one to three $C_1$–$C_4$ alkyl groups or one to three $C_1$–$C_4$ alkoxy groups,
one $C_1$–$C_6$ alkoxycarbonyl group unsubstituted or substituted with one to three halogen atoms or one to three $C_1$–$C_4$ alkoxy groups, or
one benzyloxycarbonyl group unsubstituted or substituted on the phenyl ring with one to three halogen atoms, one to three $C_1$–$C_4$ alkyl groups or one to three $C_1$–$C_4$ alkoxy groups.

4. The method according to claim 1, wherein B is $C_3$–$C_6$ alkenyl unsubstituted or substituted with one to three halogen atoms or one phenyl group.

5. The method according to claim 1, wherein B is $C_3$–$C_6$ alkynyl unsubstituted or substituted with one to three halogen atoms or one phenyl group.

6. The method according to claim 1, wherein B is

and R is ;phenyl unsubstituted or substituted with one to three halogen atoms, one or two $C_1$–$C_4$ alkyl groups, one or two $C_1$–$C_4$ alkoxy groups, $CF_3$, CN, $NO_2$, di($C_1$–$C_4$ alkyl) amino or $C_1$–$C_4$ alkanoylamino.

7. The method according to claim 1, wherein said pests are insects or acarids and are controlled by applying said compound to the foliage of plants upon which said insect or acarid pests feed.

8. The method according to claim 1, wherein said pests are mollusks and are controlled by applying said compound to the locus infested with said mollusks.

9. The method according to claim 1, wherein the compound is selected from the group consisting of
1-Methyl-2,4,5-tribromopyrrole-3-carbonitrile;
2,4,5-Tribromopyrrole-3-carbonitrile;
1-Cyano-2,4,5-tribromopyrrole-3-carbonitrile;
1-Methyl-2,4,5-trichloropyrrole-3-carbonitrile;
1-(Ethoxymethyl)-2,4,5-tribromopyrrole-3-carbonitrile;
1-Methyl-2,4,5-triiodopyrrole-3-carbonitrile;
4,5-Dibromo-2-(trifluoromethyl)pyrrole-3-carbonitrile;
4,5-Dibromo-1-methyl-2-(trifluoromethyl)pyrrole-3-carbonitrile;
2,4,5-Trichloropyrrole-3-carbonitrile;
4-Nitropyrrole-2-carbonitrile;
1-Methyl-5-nitropyrrole-2-carbonitrile;
2,4,5-Triiodopyrrole-3-carbonitrile;
1-Allyl-2,4,5-tribromopyrrole-3-carbonitrile;
2,4,5-Tribromo-1-ethylpyrrole-3-carbonitrile;
1-Benzyl-2,4,5-trichloropyrrole-3-carbonitrile;
2,4,5-Tribromopyrrole-1,3-dicarbonitrile;
2,4,5-Trichloropyrrole-1,3-dicarbonitrile;
3,4,5-Tribromo-1-methylpyrrole-2-carbonitrile;
3,4,5-Tribromopyrrole-2-carbonitrile;
5-Nitropyrrole-2-carbonitrile;
1-Ethyoxymethyl-5-nitropyrrole-2-carbonitrile;
2,3,5-Trichloro-4-nitropyrrole;
Pyrrole-2,4-dicarbonitrile;
3,4,5-Tribromo-1-(2-propynyl)pyrrole-2-carbonitrile;
2,4,5-Tribromo-1-(hydroxymethyl)pyrrole-3-carbonitrile, pivalate (ester).
2,4,5-Tribromo-1-(isopropoxymethyl)pyrrole-3-carbonitrile;
2,4,5-Tribromo-1-(2-chloro-1-ethoxyethyl)pyrrole-3-carbonitrile;
2,4,5-Tribromo-1-pyrrole-3-carbonitrile;
2,45,-Tribromo-1-(p-chlorobenzoyl)pyrrole-3-carbonitrile; and
Phenyl 2,3,5-tribromo-4-cyanopyrrole-1-carboxylate.

10. The method according to claim 7, wherein said compound is applied at a rate of about 0.125 kg/ha to 4.0 kg/ha.

11. The method according to claim 8, wherein said mollusks are aquatic, semi aquatic or terrestrial gastorpods and said compound is applied at a rate of about 0.05 kg/has to 4.0 kg/ha.

12. The method according to claim 8, wherein said mollusks are slugs or snails.

13. The method according to claim 12, wherein said slugs or snails are controlled by administering to said slugs or snails a composition containing said compound.

* * * * *